United States Patent [19]
Asao et al.

[11] Patent Number: 6,110,967
[45] Date of Patent: Aug. 29, 2000

[54] EPOXYSUCCINAMIDE DERIVATIVE OR SALT THEREOF

[75] Inventors: Tetsuji Asao, Tokorozawa; Tomohiro Yamashita, Hidaka; Yoshimitsu Suda, Tokorozawa; Shigeo Okajima, Hanno; Yukio Tada, Higashimatsuyama; Nobuhiko Katsunuma, Tokushima; Shozo Yamada, Hanno; Kazuhiko Shigeno, Iruma; Atsuhiko Uemura, Sayama, all of Japan

[73] Assignee: Taiho Pharmaceuticals Co., Ltd., Tokyo, Japan

[21] Appl. No.: 09/202,607

[22] PCT Filed: Apr. 17, 1998

[86] PCT No.: PCT/JP98/01778

§ 371 Date: Dec. 17, 1998

§ 102(e) Date: Dec. 17, 1998

[87] PCT Pub. No.: WO98/47887

PCT Pub. Date: Oct. 29, 1998

[30] Foreign Application Priority Data

Apr. 18, 1997 [JP] Japan ..................................... 9-102151

[51] Int. Cl.[7] ...................... A61K 31/495; A61K 31/435; A61K 31/41
[52] U.S. Cl. ........................ 514/475; 546/281.7; 546/207; 514/336; 514/311.1; 514/394; 514/252; 514/326; 548/311.1; 548/394; 549/548; 544/405; 544/333
[58] Field of Search ............................... 548/304.7, 311.1; 514/397, 394, 475, 252, 336, 326; 549/548; 544/333, 405; 546/281.7

[56] References Cited

U.S. PATENT DOCUMENTS 5,556,853 9/1996 Tsubotani et al. .................... 514/231.5
5,679,708 10/1997 Tsubotani et al. ...................... 514/475

FOREIGN PATENT DOCUMENTS 0 808 839 A1 11/1997 European Pat. Off. .

OTHER PUBLICATIONS

International Search Report.

Primary Examiner—Zinna Northington Davis
Assistant Examiner—Binta Robinson
Attorney, Agent, or Firm—Sughrue, Mion, Zinn, Macpeak & Seas, PLLC

[57] ABSTRACT

The invention relates an epoxysuccinamide derivative represented by a formula (I):

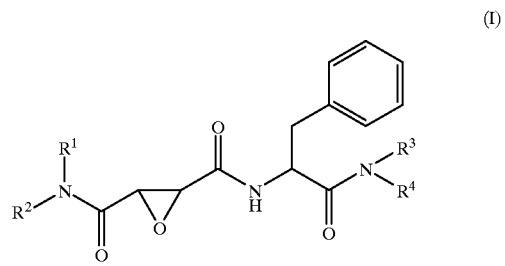

wherein $R^1$ represents a hydrogen atom, an alkyl or aminoalkyl group, $R^2$ represents an aminoalkyl group which May be substituted, an aryl group which may be substituted, a heterocyclic group which may be substituted, an aralkyl group which may be substituted, or an alkyl group substituted by a heterocyclic ring which may be substituted, or $R^1$ and $R^2$ may form a nitrogen-containing heterocyclic ring, which may be substituted, together with the adjacent nitrogen atoms, and $R^3$ and $R^4$ are the same or different from each other and independently represent a hydrogen atom, or an alkyl or aralkyl group, or a salt thereof, a preparation process thereof, and a medicine comprising such a derivative or salt as an active ingredient. This compound has a specific inhibitory activity for cathepsin L and family enzymes thereof, and is useful as an agent for preventing and treating metabolic osteopathy such as osteoporosis and hypercalcemia.

23 Claims, No Drawings

EPOXYSUCCINAMIDE DERIVATIVE OR SALT THEREOF

This application is filed under 35 U.S.C. § 371 based on PCT/JP98/01778, filed Apr. 17, 1998.

TECHNICAL FIELD

The present invention relates to novel epoxysuccinamide derivatives or salts thereof, which have inhibitory activity against cathepsin, and medicines comprising such a derivative or salt.

BACKGROUND ART

On the current trend toward the aging society, abnormal acceleration of bone resorption in a human advanced in years involves many of various senile diseases. In particular, senile osteoporosis is prominent and about to become a great social problem. When the present pharmacotherapy for this senile osteoporosis is viewed, it is conducted to administer (1) estrogen, (2) protein anabolic hormones, (3) calcitonin, (4) vitamin D or (5) bisphosphonates. However, their effects are found only in improvement of subjective symptom, and hence there is no critical therapy under the circumstances.

On the other hand, it is considered that factors causing osteoporosis include two of calcification and decalcification, and abnormal decomposition of supporting tissue, collagen. However, the development of pharmaceutical agents by paying attention to the abnormal acceleration of collagen decomposition is only now under way. It is reported that a group of cathepsins takes part in this collagen decomposition to the greatest extent, and cathepsin L among the group of cathepsins, which belongs to cysteine proteases, particularly deeply involves the collagen decomposition [FEBS Letters, 269, pp. 189–193 (1990); and FEBS Letters, 280, pp. 311–315 (1991)]. It has recently be found that cathepsin K, which is a family enzyme of cathepsin L, also takes parts in bone resorption [J. Biol. Chem., 271, pp. 12517–12524 (1996)]. With respect to compounds which inhibit cysteine proteases, epoxysuccinic acid derivatives similar to those of the present application have been reported in, for example, Japanese Patent Application Laid-Open No. 104683/1996 and European Patent Publication No. 655447A1. However, these compounds inhibit both enzymes of cathepsin L and cathepsin B without any selectivity. It has been reported that cathepsin B does not take part in bone resorption [FEBS Letters, 321, pp. 247–250 (1993)], and is an enzyme related to an immune system such as antigen presenting [FEBS Letters, 324, pp. 325–330 (1993)]. It is hence apprehended that immunodeficiency may be caused if cathepsin B is inhibited. In order to inhibit bone resorption selectively, it is therefore necessary to use an inhibitor which selectively inhibits cathepsin L and family enzymes thereof. However, such a selective inhibitor has not been found yet.

It is an object of the present invention to provide a novel compound which inhibits cathepsin L and its family enzymes at a concentration lower than against other cysteine proteases, and in other words, a novel compound useful as an agent for treating and preventing metabolic osteopathy such as osteoporosis, hypercalcemia, Paget's disease, hyperparathyroidism and bone metastasis of cancer.

DISCLOSURE OF THE INVENTION

In order to achieve the above object, the present inventors have synthesized a great number of epoxysuccinamide derivatives and evaluated their action on cathepsins. As a result, the inventors have succeeded in inventing compounds which specifically inhibit cathepsin L and are useful as medicines such as agents for treating osteoporosis, thus leading to completion of the present invention.

Namely, the present invention provides an epoxysuccinamide derivative represented by a formula (I):

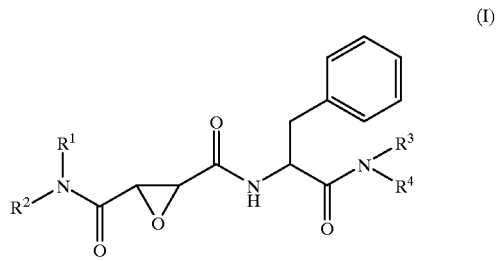

(I)

wherein $R^1$ represents a hydrogen atom, an alkyl group or an aminoalkyl group which may have a protecting group, $R^2$ represents an aminoalkyl group which may be substituted, an aryl group which may be substituted, an aralkyl group which may be substituted, a heterocyclic group which may be substituted, or an alkyl group substituted by a heterocyclic ring which may be substituted, or $R^1$ and $R^2$ may form a nitrogen-containing heterocyclic ring, which may be substituted, together with the adjacent nitrogen atoms, and $R^3$ and $R^4$ are the same or different from each other and independently represent a hydrogen atom, or an alkyl or aralkyl group, or a salt thereof, and a preparation process thereof.

The present invention also provides a medicine comprising an epoxysuccinamide derivative represented by the formula (1) or a salt thereof as an active ingredient.

The present invention further provides a medicinal composition comprising an epoxysuccinamide derivative represented by the formula (1) or a salt thereof and a pharmaceutically acceptable carrier.

The present invention still further provides use of an epoxysuccinamide derivative represented by the formula (1) or a salt thereof for a medicine.

The present invention yet still further provides a method of treating osteopathy, which comprises administering an effective amount of an epoxysuccinamide derivative represented by the formula (1) or a salt thereof.

BEST MODE FOR CARRYING OUT THE INVENTION

In the formula (I), the alkyl group represented by $R^1$ is preferably an alkyl group having 1 to 6 carbon atoms, and examples thereof include methyl, ethyl, propyl, isopropyl, butyl, isobutyl, pentyl, isopentyl, hexyl and isohexyl groups.

The aminoalkyl group represented by $R^1$ is preferably an aminoalkyl group having 1 to 6 carbon atoms, and examples thereof include aminomethyl, aminoethyl, aminopropyl, aminobutyl, aminopentyl and aminohexyl groups. The amino group of the aminoalkyl group may be protected by an alkyloxycarbonyl group having 2 to 7 carbon atoms in total, such as a tert-butoxycarbonyl group.

Of these, the hydrogen atom, $C_{1-6}$ alkyl group or $C_{1-6}$ aminoalkyl group is more preferred as $R^1$, with the hydrogen atom, methyl group or aminoethyl group being particularly preferred.

In the formula (I), the aminoalkyl group represented by $R^2$ is preferably an aminoalkyl group having 1 to 6 carbon atoms, and examples thereof include aminomethyl, aminoethyl, aminopropyl, aminoisopropyl, aminobutyl, aminoisobutyl, aminopentyl, aminoisopentyl, aminohexyl and aminoisohexyl groups. Of these, the aminoethyl group is particularly preferred. These aminoalkyl groups may have a substituent group on their amino groups. Examples of the substituent group include alkyloxycarbonyl groups (methoxycarbonyl group, ethoxycarbonyl group, propoxycarbonyl group, isopropoxycarbonyl group, butoxycarbonyl group, tert-butoxycarbonyl group, pentyloxycarbonyl group, hexyloxycarbonyl group, etc.) having 2 to 7 carbon atoms in total, aralkyloxycarbonyl groups (benzyloxycarbonyl group, phenylethyloxycarbonyl group, phenylpropyloxycarbonyl group, naphthylmethyloxycarbonyl group, etc.) having 8 to 14 carbon atoms in total, alkylsulfinyl groups (methylsulfinyl group, ethylsulfinyl group, propylsulfinyl group, butylsulfinyl group, pentylsulfinyl group, hexylsulfinyl group, etc.) having 1 to 6 carbon atoms, alkylsulfonyl groups (methylsulfonyl group, ethylsulfonyl group, propylsulfonyl group, butylsulfonyl group, pentylsulfonyl group, hexylsulfonyl group, etc.) having 1 to 6 carbon atoms, arylsulfinyl groups (benzenesulfinyl group, toluenesulfinyl group, naphthalenesulfinyl group, etc.) having 6 to 10 carbon atoms, arylsulfonyl groups (benzenesulfonyl group, toluenesulfonyl group, naphthalenesulfonyl group, etc.) having 6 to 10 carbon atoms, and heterocyclic groups (pyridyl group, nitropyridyl group, aminopyridyl group, aminopyrimidyl group, etc.) which may be substituted by an amino or nitro group.

Of these substituted aminoalkyl groups, $C_{1-6}$ aminoalkyl groups substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group) are preferred, and aminoethyl groups substituted by a heterocyclic group (which may be substituted further by an amino or nitro group) are more preferred, with an aminoethyl group substituted by a pyridyl or primidyl group (which may be substituted further by an amino or nitro group) being particularly preferred.

In the formula (I), the aryl group represented by $R^2$ is preferably an aryl group having 6 to 10 carbon atoms, and examples thereof include phenyl and naphthyl groups. Of these, the phenyl group is more preferred. These aryl groups may have 1 to 3 substituent groups at optional positions thereof. Examples of the substituent groups include aryloxy groups (phenoxy group, naphthyloxy group, etc.) having 6 to 10 carbon atoms, a hydroxyl group, an amino group, an amidino group, an acetoamidino group, a guanidino group, a cyano group, a carboxyl group, aralkyloxycarbonyl groups (benzyloxycarbonyl group, phenylethyloxycarbonyl group, phenylpropyloxycarbonyl group, naphthylmethyloxycarbonyl group, etc.) having 8 to 14 carbon atoms in total, a carbamoyl group, an acyl group, an acylamino group, a 1-piperidino group, a 1-piperazino group, a 5-nitropyridin-2-yl group, alkyloxycarbonylamino groups (methoxycarbonylamino group, ethoxycarbonylamino group, propoxycarbonylamino group, isopropoxycarbonylamino group, butoxycarbonylamino group, tert-butoxycarbonylamino group, pentyloxycarbonylamino group, hexyloxycarbonylamino group, etc.) having 2 to 7 carbon atoms in total, aralkyloxycarbonylamino groups (benzyloxycarbonylamino group, phenylethyloxycarbonylamino group, phenylpropyloxycarbonylamino group, naphthylmethyloxycarbonylamino group, etc.) having 8 to 14 carbon atoms in total, alkylthio groups (methylthio group, ethylthio group, propylthio group, butylthio group, pentylthio group, hexylthio group, etc.) having 1 to 6 carbon atoms, alkylsulfinyl groups (methylsulfinyl group, ethylsulfinyl group, propylsulfinyl group, butylsulfinyl group, pentylsulfinyl group, hexylsulfinyl group, etc.) having 1 to 6 carbon atoms, aminosulfonyl group, alkylsulfonyl groups (methylsulfonyl group, ethylsulfonyl group, propylsulfonyl group, butylsulfonyl group, pentylsulfonyl group, hexylsulfonyl group, etc.) having 1 to 6 carbon atoms, arylthio groups (phenylthio group, naphthylthio group, etc.) having 6 to 10 carbon atoms, arylsulfinyl groups (benzenesulfinyl group, toluenesulfinyl group, naphthalenesulfinyl group, etc.) having 6 to 10 carbon atoms, arylsulfonyl groups (benzenesulfonyl group, toluenesulfonyl group, naphthalenesulfonyl group, etc.) having 6 to 10 carbon atoms, arylsulfonylamino groups (benzenesulfonylamino group, toluenesulfonylamino group, naphthalenesulfonylamino group, etc.) having 6 to 10 carbon atoms, alkyl groups (methyl group, ethyl group, propyl group, isopropyl group, butyl group, isobutyl group, tert-butyl group, pentyl group, isopentyl group, neopentyl group, hexyl group, isohexyl group, etc.) which have 1 to 6 carbon atoms and may be substituted, and alkenyl groups (ethenyl group, propenyl group, butenyl group, pentenyl group, hexenyl group, etc.) having 2 to 6 carbon atoms. Examples of a substituent group that the alkyl groups as such substituent groups may further have include a hydroxyl group, an amino group, acylamino groups (acetylamino group, propanoylamino group, benzoylamino group, etc.), alkyloxycarbonylamino groups having 2 to 7 carbon atoms in total, aralkyloxycarbonylamino groups having 8 to 14 carbon atoms in total, and protected amino groups such as $C_{6-10}$ arylsulfonylamino groups.

Of these aryl groups which may be substituted, phenyl groups substituted by groups selected from a carboxyl group, aralkyloxycarbonyl groups having 8 to 14 carbon atoms in total, $C_{1-6}$ alkyl groups substituted by an alkyloxycarbonylamino group having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups are more preferred. Of these, phenyl groups substituted by groups selected from a carboxyl group, $C_{1-6}$ alkyl groups, $C_{2-6}$ alkenyl groups, benzoylamino-substituted $C_{1-6}$ alkyl groups, aryloxy groups having 6 to 10 carbon atoms and $C_{1-6}$ aminoalkyl groups are more preferred, with phenyl groups substituted by groups selected from aminomethyl, ethyl, tert-butyl, carboxyl, benzoylaminomethyl, vinyl and phenoxy groups being particularly preferred.

In the formula (I), the aralkyl group represented by $R^2$ is preferably an aralkyl group having 7 to 12 carbon atoms, and examples thereof include phenyl-$C_{1-6}$-alkyl groups such as benzyl, phenethyl, phenylpropyl and phenylbutyl groups. Examples of the substituent group of such an aralkyl group include the same groups as the substituent groups of the aryl group which is represented by $R^2$ and may be substituted. Of these aralkyl groups, phenyl-$C_{1-6}$-alkyl groups which may be substituted by a group selected from acetoamidino, methylsulfonyl, aminosulfonyl, carbamoyl and amino groups are more preferred, and phenyl-$C_{1-3}$-alkyl groups which may be substituted by a group selected from acetoamidino, aminosulfonyl and amino groups are further preferred, with a benzyl or phenethyl group which may be substituted by a group selected from acetoamidino, aminosulfonyl and amino groups being particularly preferred.

In the formula (I), the heterocyclic group represented by $R^2$ is preferably a saturated or unsaturated heterocyclic group which has a 5- to 10-membered monocyclic or fused ring having, as heteroatom(s), 1 to 3 atoms selected from nitrogen, oxygen and sulfur. Examples thereof include piperidinyl, pyrrolyl, imidazolyl, pyrazolyl, furyl, thienyl, oxazolyl, isoxazolyl, thiazolyl, isothiazolyl, furazanyl, pyridyl, pyrazinyl, pyrimidinyl, pyridazinyl, triazinyl, quinolyl, isoquinolyl and benzimidazolyl groups. Examples of the substituent group of such a heterocyclic group include the same groups as the substituent groups of the aryl group which is represented by $R^2$ and may be substituted. Of these, a phenyl-$C_{1-6}$-alkyl group or $C_{1-6}$ alkyl group is preferred.

Of these heterocyclic groups which may be substituted, piperidinyl, pyridyl, quinolyl and isoxazolyl groups which may be substituted by a phenyl-$C_{1-6}$-alkyl group or $C_{1-6}$ alkyl group are preferred, and piperidinyl, pyridyl and isoxazolyl groups which may be substituted by a phenyl-$C_{1-6}$-alkyl group or $C_{1-6}$ alkyl group are more preferred, with piperidinyl, pyridyl and isoxazolyl groups which may be substituted by a benzyl or methyl group being particularly preferred.

In the formula (I), examples of the alkyl group substituted by a heterocyclic group represented by $R^2$ include $C_{1-6}$ alkyl groups substituted by a nitrogen-containing saturated heterocyclic ring such as a morpholino, piperidinyl or piperazinyl group, and $C_{1-6}$ alkyl groups substituted by an aromatic heterocyclic ring composed of a 5- to 10-membered monocyclic or fused ring having, as heteroatom(s), 1 to 3 atoms selected from nitrogen, oxygen and sulfur. Examples of the aromatic heterocyclic groups in $C_{1-6}$ alkyl groups substituted by an aromatic heterocyclic group include pyrrolyl, imidazolyl, pyrazolyl, furyl, thienyl, oxazolyl, isoxazolyl, thiazolyl, isothiazolyl, furazanyl, pyridyl, pyrazinyl, pyrimidinyl, pyridazinyl, triazinyl, quinolyl, isoquinolyl, benzimidazolyl, naphthyridinyl, phthalazinyl, indolyl, benzofuranyl, benzotriazolyl and benzoxazolyl groups. Examples of the $C_{1-6}$ alkyl groups include methyl, ethyl and n-propyl groups. Examples of the substituent group of such a heterocyclic ring include the same groups as the substituent groups of the aryl group which is represented by $R^2$ and may be substituted.

Of these heterocyclic group-substituted alkyl groups, $C_{1-6}$ alkyl groups substituted by a heterocyclic group selected from piperidinyl, morpholino, thiazolyl, imidazolyl, pyrrolyl, pyridyl, pyrazinyl, pyrimidinyl and benzimidazolyl groups (which may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group) are more preferred, with $C_{1-6}$ alkyl groups substituted by a heterocyclic group selected from morpholino, thiazolyl, imidazolyl, pyridyl, pyrazinyl and benzimidazolyl groups (which may be substituted by 1 to 3 groups selected from an amino group, a dimethylpyrrolyl group, $C_{1-6}$ alkyl groups and a nitro group) being particularly preferred.

In the formula (I), the nitrogen-containing heterocyclic ring that is formed by $R^1$ and $R^2$ together with the adjacent nitrogen atom and may be substituted is preferably a 5-, 6- or 7-membered ring having, as heteroatom(s), 1 to 3 atoms selected from nitrogen, oxygen and sulfur. Examples thereof include pyrrolidine, imidazolidine, piperidine, piperazine and morpholine. Examples of the substituent group of such a heterocyclic group include the same groups as the substituent groups of the aryl group which is represented by $R^2$ and may be substituted. Of these, a phenyl group, phenyl-$C_{1-6}$-alkyl groups, alkyloxycarbonyl groups having 2 to 7 carbon atoms in total, methylenedioxyphenyl-$C_{1-6}$-alkyl groups, a pyrimidinyl group and an aminopyrimidinyl group are more preferred.

Of these nitrogen-containing heterocyclic rings, a piperazine ring which may be substituted by a group selected from phenyl, phenyl-$C_{1-6}$-alkyl, methylene-dioxyphenyl-$C_{1-6}$-alkyl, pyrimidinyl and aminopyrimidinyl groups is preferred, with a piperazine ring having a substituent group selected from methylenedioxybenzyl, pyrimidinyl and aminopyrimidinyl groups being particularly preferred.

In the formula (I), the alkyl groups represented by $R^3$ and $R^4$ include the same $C_{1-6}$-alkyl groups as the examples of the alkyl group represented by $R^1$. Of these, methyl, ethyl and n-propyl groups are preferred with methyl being particularly preferred.

In the formula (I), the aralkyl groups represented by $R^3$ and $R^4$ include the same phenyl-$C_{1-6}$-alkyl groups as the examples of the aralkyl group which may be substituted, represented by $R^2$. Of these, benzyl and phenethyl groups are particularly preferred.

The epoxysuccinamide derivatives according to the present invention can form pharmaceutically acceptable salts. As specific examples thereof, alkali and alkaline earth metal salts such as the lithium salt, sodium salt, potassium salt, magnesium salt and calcium salt, or ammonium salts such as the ammonium salt, methylammonium salt, dimethylammonium salt and trimethylammonium salt may be formed when an acid group is present. When a basic group is present, mineral acid salts such as the hydrochloride, hydrobromide, sulfate, nitrate and phosphate; or organic acid salts such as the acetate, propionate, tartarate, fumarate, maleate, malate, citrate, methanesulfonate and p-toluenesulfonate may be formed. The epoxysuccinamide derivatives according to the present invention may be present in the form of hydrates.

With respect to the stereochemistry as to the epoxy moieties of the epoxysuccinamide derivatives according to the present invention represented by the formula (I), four configurations of (R,R), (S,R), (R,S) and (S,S) can be taken depending on the configuration of epoxysuccinic acid used as a starting material. The present invention include all of these configurations. With respect to asymmetric carbon atoms other than the above, both R and S are included.

In the compounds according to the present invention, more preferred are compounds in which $R^1$ is a hydrogen atom, or a $C_{1-6}$ alkyl or $C_{1-6}$ aminoalkyl group, $R^2$ is an amino-$C_{1-6}$-alkyl group which may be substituted, a phenyl group which may be substituted, a heterocyclic group which may be substituted, a phenyl-$C_{1-6}$-alkyl group which may be substituted, or a $C_{1-6}$ alkyl group substituted by a heterocyclic ring which may be substituted, or $R^1$ and $R^2$ form a nitrogen-containing heterocyclic ring, which may be substituted, together with the adjacent nitrogen atom; and $R^3$ and $R^4$ are independently a hydrogen atom, or a $C_{1-6}$ alkyl or phenyl-$C_{1-6}$-alkyl group.

With respect to $R^2$, more preferred compounds are those in which $R^2$ is a group selected from (1) a $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group substituted by groups selected from a carboxyl group, aralkyloxycarbonyl groups having 8 to 14 carbon atoms in total, $C_{1-6}$ alkyl groups substituted by an alkyloxycarbonylamino group having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl, carbamoyl and amino groups; (4) a saturated or unsaturated heterocyclic group which may be substituted by a phenyl-$C_{1-6}$-alkyl or $C_{1-6}$ alkyl group and has a 5- to 10-membered monocyclic or fused ring having, as heteroatom(s), 1 to 3 atoms selected from nitrogen, oxygen and sulfur; and (5) a $C_{1-6}$ alkyl group substituted by a nitrogen-containing saturated heterocyclic ring or an aromatic heterocyclic ring composed of a 5- to 10-membered monocyclic or fused ring having, as heteroatom(s), 1 to 3 atoms selected from nitrogen, oxygen and sulfur (which the aromatic heterocyclic ring may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or in which $R^1$ and $R^2$ form, together with the adjacent nitrogen atom, a piperazine ring which may be substituted by a group selected from phenyl, phenyl-$C_{1-6}$-alkyl, methylenedioxyphenyl-$C_{1-6}$-alkyl, pyrimidinyl and aminopyrimidinyl groups.

With respect to $R^3$ and $R^4$, preferred compounds are those in which both $R^3$ and $R^4$ are $C_{1-6}$ alkyl groups, or $R^3$ is a hydrogen atom, and $R^4$ is a $C_{1-6}$ alkyl or phenyl-$C_{1-6}$-alkyl group.

Specific examples of preferred compounds according to the present invention are shown in the following Tables 1 to 8.

TABLE 1

| Compound No. | R1 | R2 | (*,*,*) | R³ | R⁴ |
|---|---|---|---|---|---|
| 1 | | phenyl-piperidine | S,S,S | —CH₃ | —CH₃ |
| 2 | H | PhSO₂NH-propyl | S,S,S | —CH₃ | —CH₃ |
| 3 | H | BocHN-CH₂-(2-methylphenyl) | S,S,S | —CH₃ | —CH₃ |
| 4 | H | HCl·H₂N-CH₂-(2-methylphenyl) | S,S,S | —CH₃ | —CH₃ |
| 5 | H | BocHN-CH₂-(3-methylphenyl) | S,S,S | —CH₃ | —CH₃ |
| 6 | H | HCl·H₂N-CH₂-(3-methylphenyl) | S,S,S | —CH₃ | —CH₃ |

TABLE 1-continued
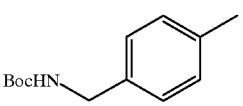
| Compound No. | R¹ | R² | (*,*,*) | R³ | R⁴ |
|---|---|---|---|---|---|
| 7 | H | 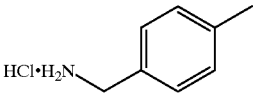 | S,S,S | —CH₃ | —CH₃ |
| 8 | H | 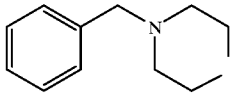 | S,S,S | —CH₃ | —CH₃ |
| 9 | | 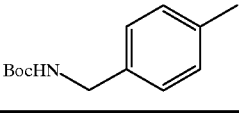 | S,S,S | —CH₃ | —CH₃ |
| 10 | BocHN—CH₂CH₂— | Ph | S,S,S | —CH₃ | —CH₃ |
| 11 | HCl·H₂N—CH₂CH₂— | Ph | S,S,S | —CH₃ | —CH₃ |
| 12 | H | 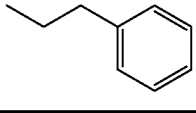 | S,S,S | H | 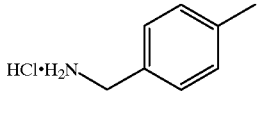 |
TABLE 2
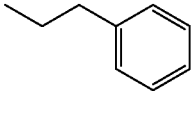
| Compound No. | R¹ | R² | (*,*,*) | R³ | R⁴ |
|---|---|---|---|---|---|
| 13 | H | 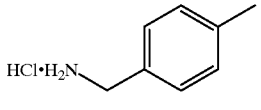 | S,S,S | H | 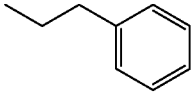 |
| 14 | H | 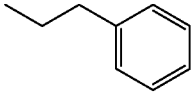 | S,S,S | —CH₃ | 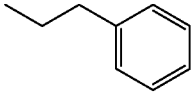 |

TABLE 2-continued

| Compound No. | R[1] | R[2] | (*,*,*) | R[3] | R[4] |
|---|---|---|---|---|---|
| 15 | | Boc-N-piperidine | S,S,S | —CH$_3$ | —CH$_3$ |
| 16 | | HCl·HN-piperidine | S,S,S | —CH$_3$ | —CH$_3$ |
| 17 | | tetrahydropyran (O-containing ring) | S,S,S | —CH$_3$ | —CH$_3$ |
| 18 | H | 1-benzyl-4-methylpiperidine · HCl | S,S,S | —CH$_3$ | —CH$_3$ |
| 19 | H | 1-propylpiperidine · HCl | S,S,S | —CH$_3$ | —CH$_3$ |
| 20 | H | HCl·H$_2$N—C$_6$H$_4$—ethyl | S,S,S | —CH$_3$ | —CH$_3$ |
| 21 | H | H$_2$N—SO$_2$—C$_6$H$_4$—CH$_3$ | S,S,S | —CH$_3$ | —CH$_3$ |
| 22 | H | CbzHNCH$_2$CH$_2$— | S,S,S | —CH$_3$ | —CH$_3$ |
| 23 | H | BocHNCH$_2$CH$_2$— | S,S,S | —CH$_3$ | —CH$_3$ |
| 24 | H | HCl·H$_2$NCH$_2$CH$_2$— | S,S,S | —CH$_3$ | —CH$_3$ |
| 25 | | benzodioxole-CH$_2$-cyclohexyl-propyl | S,S,S | —CH$_3$ | —CH$_3$ |

TABLE 3

[Structure: epoxide core with R¹R²N-C(=O)- and -C(=O)-NH-CH(CH₂Ph)(CH₂-CR³R⁴) substituents, with three stereocenters marked *]

| Compound No. | R¹ | R² | (*,*,*) | R³ | R⁴ |
|---|---|---|---|---|---|
| 26 | H | BocHN-CH₂-(4-phenyl)- | S,S,S | H | —CH₂CH₂CH₃ |
| 27 | H | HCl·H₂N-CH₂-(4-phenyl)- | S,S,S | H | —CH₂CH₂CH₃ |
| 28 | H | Me-(4-phenyl)- | S,S,S | —CH₃ | —CH₃ |
| 29 | H | Et-(4-phenyl)- | S,S,S | —CH₃ | —CH₃ |
| 30 | H | (CH₃)₂CH-(4-phenyl)- | S,S,S | H | —CH₃ |
| 31 | —CH₃ | Et-(4-phenyl)- | S,S,S | —CH₃ | —CH₃ |
| 32 | H | Et-(4-phenyl)- | S,S,S | H | —CH₂CH₂CH₃ |
| 33 | H | (CH₃)₂CH-(4-phenyl)- | S,S,S | H | —CH(CH₃)₂ |
| 34 | H | Et-(4-phenyl)- | S,S,S | H | —CH₂CH₂-phenyl |
| 35 | H | phenyl- | S,S,S | —CH₃ | —CH₃ |

TABLE 3-continued

[Structure: R¹R²N-C(O)-[oxirane with two *]-C(O)-NH-C*H(CH₂Ph)-CH₂-C(R³)(R⁴)]

| Compound No. | R₁ | R² | (*,*,*) | R³ | R⁴ |
|---|---|---|---|---|---|
| 36 | H | 3-pyridyl ·HCl | S,S,S | —CH₃ | —CH₃ |
| 37 | H | 4-tert-butylphenyl | S,S,S | —CH₃ | —CH₃ |

TABLE 4

[Structure: R¹R²N-C(O)-[oxirane with two *]-C(O)-NH-C*H(CH₂Ph)-C(O)-NR³R⁴]

| Compound No. | R¹ | R² | (*,*,*) | R³ | R⁴ |
|---|---|---|---|---|---|
| 38 | H | 2-(BocHN)-4-propylthiazole | S,S,S | —CH₃ | —CH₃ |
| 39 | H | 2-(H₂N·HCl)-4-propylthiazole | S,S,S | —CH₃ | —CH₃ |
| 40 | H | 6-quinolyl ·HCl | S,S,S | —CH₃ | —CH₃ |

TABLE 4-continued
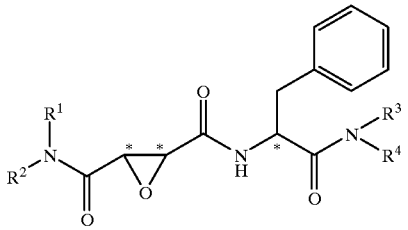
| Compound No. | R¹ | R² | (*,*,*) | R³ | R⁴ |
|---|---|---|---|---|---|
| 41 | H | 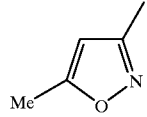 | S,S,S | —CH₃ | —CH₃ |
| 42 | H | 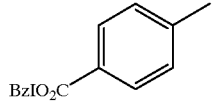 | S,S,S | —CH₃ | —CH₃ |
| 43 | H | 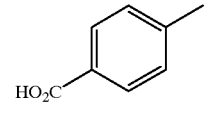 | S,S,S | —CH₃ | —CH₃ |
| 44 | H | 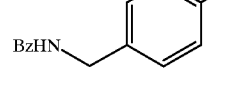 | S,S,S | —CH₃ | —CH₃ |
| 45 | H | 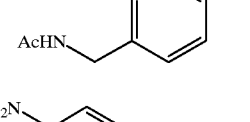 | S,S,S | —CH₃ | —CH₃ |
| 46 | H | 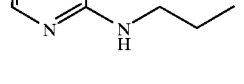 | S,S,S | —CH₃ | —CH₃ |
| 47 | H | 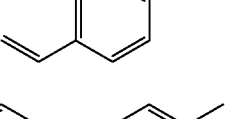 | S,S,S | —CH₃ | —CH₃ |
| 48 | H | 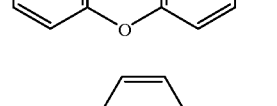 | S,S,S | —CH₃ | —CH₃ |
| 49 | H | 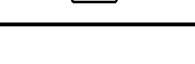 | R,R,S | —CH₃ | —CH₃ |

TABLE 5
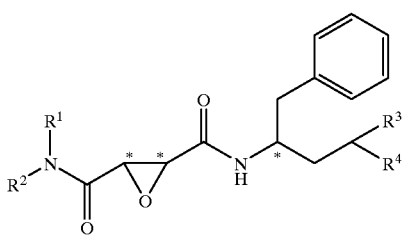
| Compound No. | R[1] | R[2] | (*,*,*) | R[3] | R[4] |
|---|---|---|---|---|---|
| 50 | H | 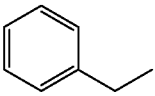 | S,S,S | —CH₃ | —CH₃ |
| 51 | H | 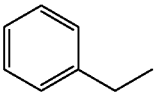 | S,S,S | —CH₃ | —CH₃ |
| 52 | H | 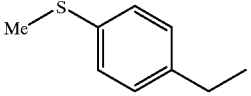 | S,S,S | H | —CH₂CH₃ |
| 53 | H | 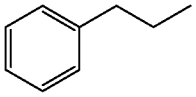 | S,S,S | —CH₃ | —CH₃ |
| 54 | H | 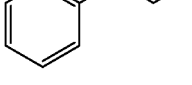 | S,S,S | H | —CH₃ |
| 55 | H | 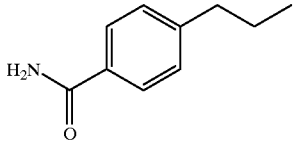 | S,S,S | H | —CH₂CH₂CH₃ |
| 56 | H | 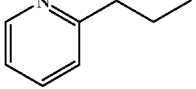 | S,S,S | —CH₃ | —CH₃ |
| 57 | H | 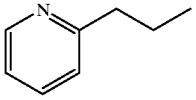 | S,S,S | H | —CH₂CH₂CH₃ |
| 58 | H | 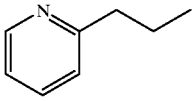 | S,S,S | H | —CH(CH₃)₂ |

TABLE 5-continued

| Compound No. | R¹ | R² | (*,*,*) | R³ | R⁴ |
|---|---|---|---|---|---|
| 59 | H | 2-pyridyl-propyl | S,S,S | H | phenylpropyl |
| 60 | H | phenylpropyl | R,R,S | —CH₃ | —CH₃ |
| 61 | H | 2-pyridyl-propyl | R,R,S | —CH₃ | —CH₃ |

TABLE 6

| Compound No. | R¹ | R² | (*,*,*) | R³ | R⁴ |
|---|---|---|---|---|---|
| 62 | H | 2-pyridyl-propyl | S,S,S | H | —CH₃ |
| 63 | H | 4-imidazolyl-propyl | S,S,S | —CH₃ | —CH₃ |
| 64 | —CH₃ | 2-pyridyl-propyl | S,S,S | —CH₃ | —CH₃ |

TABLE 6-continued
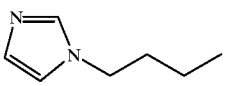
| Compound No. | R[1] | R[2] | (*,*,*) | R[3] | R[4] |
|---|---|---|---|---|---|
| 65 | H | 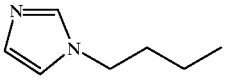 | S,S,S | —CH$_3$ | —CH$_3$ |
| 66 | H | 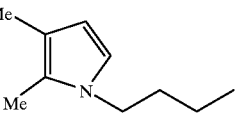 | S,S,S | H | —CH$_3$ |
| 67 | H | 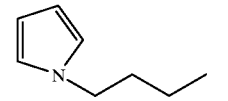 | S,S,S | H | —CH$_2$CH$_2$CH$_3$ |
| 68 | H | 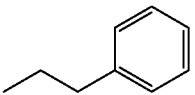 | S,S,S | H | 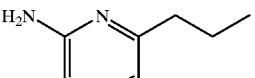 |
| 69 | H | 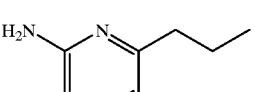 | S,S,S | —CH$_3$ | —CH$_3$ |
| 70 | H | 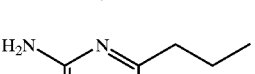 | S,S,S | H | —CH$_3$ |
| 71 | H | 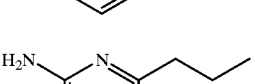 | S,S,S | H | —CH$_2$CH$_2$CH$_3$ |
| 72 | H | 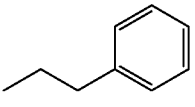 | S,S,S | H | 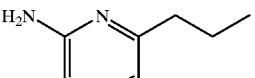 |
| 73 | H | 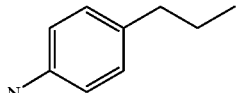 | S,S,S | —CH$_3$ | —CH$_3$ |

TABLE 7
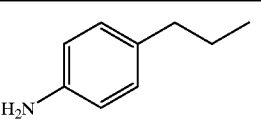
| Compound No. | R¹ | R² | (*,*,*) | R³ | R⁴ |
|---|---|---|---|---|---|
| 74 | H | 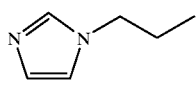 | S,S,S | H | —CH₂CH₂CH₃ |
| 75 | H | 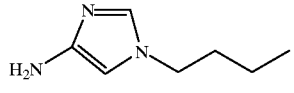 | S,S,S | —CH₃ | —CH₃ |
| 76 | H | 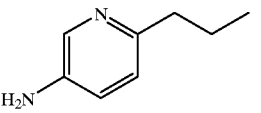 | S,S,S | —CH₃ | —CH₃ |
| 77 | H | 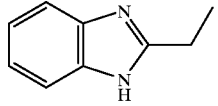 | S,S,S | —CH₃ | —CH₃ |
| 78 | H | 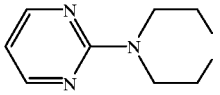 | S,S,S | —CH₃ | —CH₃ |
| 79 | | 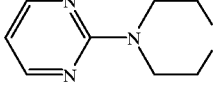 | S,S,S | —CH₃ | —CH₃ |
| 80 | | 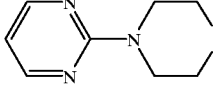 | S,S,S | H | —CH₂CH₂CH₃ |
| 81 | | 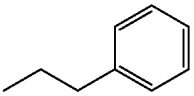 | S,S,S | H | 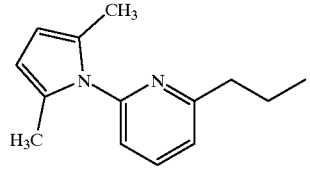 |
| 82 | H | 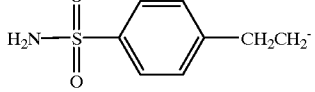 | S,S,S | —CH₃ | —CH₃ |
| 83 | H |  | S,S,S | —CH₃ | —CH₃ |

TABLE 7-continued
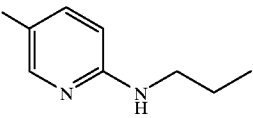
| Compound No. | R¹ | R² | (*,*,*) | R³ | R⁴ |
|---|---|---|---|---|---|
| 84 | H | H₂N—(5-pyridyl)-NH-propyl | S,S,S | —CH₃ | —CH₃ |
TABLE 8
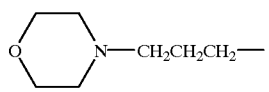
| Compound No. | R¹ | R² | (*,*,*) | R³ | R⁴ |
|---|---|---|---|---|---|
| 85 | H | morpholine-N—CH₂CH₂CH₂— | S,S,S | —CH₃ | —CH₃ |
| 86 | H | ·HBr, HN=C(CH₃)—NH—(4-C₆H₄)—propyl | S,S,S | —CH₃ | —CH₃ |
| 87 | H | 2-methyl-5-nitro-1-butyl-imidazole | S,S,S | —CH₃ | —CH₃ |
| 88 | H | 2-propyl-pyrazine | S,S,S | —CH₃ | —CH₃ |
| 89 | H | 2-propyl-pyrimidine | S,S,S | —CH₃ | —CH₃ |

TABLE 8-continued

[Structure of compound with R¹, R², R³, R⁴ substituents on epoxysuccinyl-phenylalanine amide scaffold]

| Compound No. | R¹ | R² | (*,*,*) | R³ | R⁴ |
|---|---|---|---|---|---|
| 90 | | [4-amino-2-(piperidin-1-yl)pyrimidine, H₂N-pyrimidine-piperidine] | | | |
| 91 | | [4-amino-2-(piperidin-1-yl)pyrimidine] | S,S,S | H | —CH₂CH₂CH₃ |
| 92 | | [4-amino-2-(piperidin-1-yl)pyrimidine] | S,S,S | H | —CH₂CH₂-phenyl |
| 93 | H | [4-amino-2-(propylamino)pyrimidine] | S,S,S | —CH₃ | —CH₃ |

Ac: Acetyl
Bz: Benzoyl
Cbz: Benzyloxycarbonyl
Boc: tert-butoxycarbonyl
Bzl: Benzyl
Ph: Phenyl Of the compounds shown in the above tables, Compounds 8, 11, 13, 18, 25, 27, 29, 31, 32, 35, 37, 39, 40, 41, 43, 44, 46 to 50, 53, 56, 62 to 65, 69, 73, 75 to 79, 82 to 88, 90, and 93 are more preferred from the viewpoints of selectivity of inhibitory activity against cathepsin L and its family enzymes, inhibitory action on bone resorption, and in vivo stability. Compounds 8, 11, 13, 27, 29, 31, 32, 49, 53, 56, 65, 69, 73, 75, 77, 79, 90 and 93 are more preferred, with Compounds 56, 65, 75, 79 and 90 being particularly preferred.

The epoxysuccinic acid derivatives according to the present invention can be synthesized in accordance with, for example, the following process.

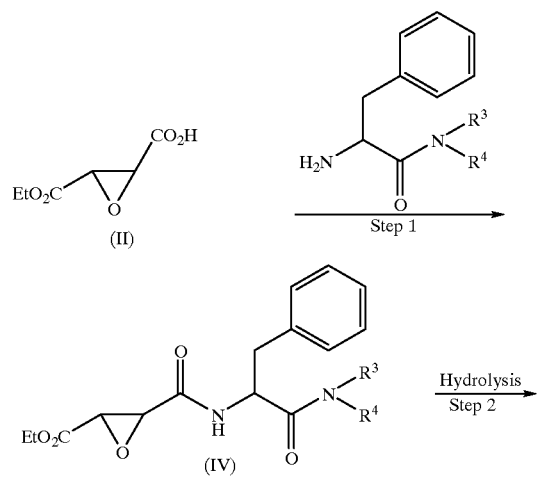

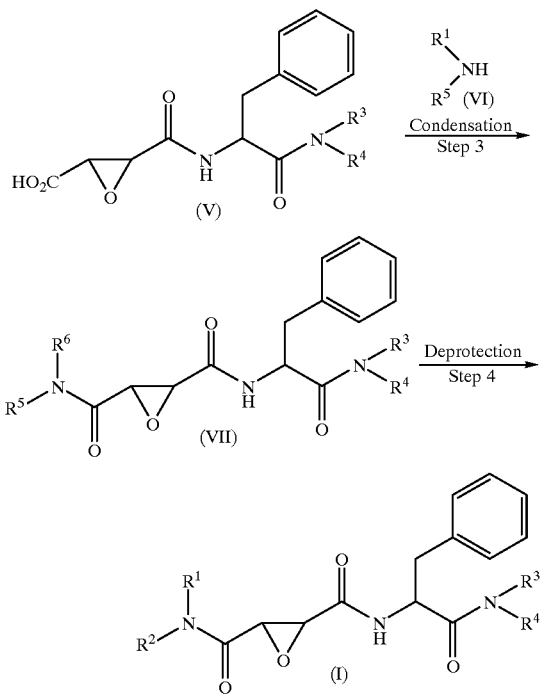

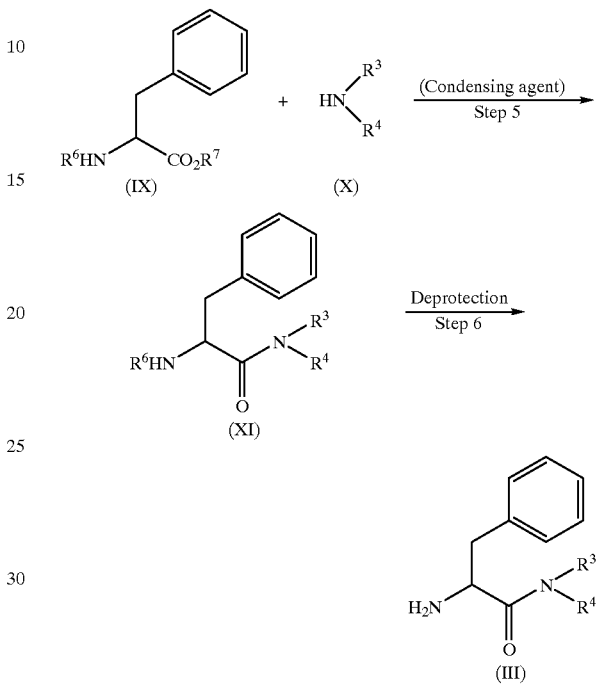

[wherein in the individual formulae, $R^1$, $R^2$, $R^3$ and $R^4$ have the same meanings as defined above, and $R^5$ is a protected $R^2$ which is used in the case where a substituent group of $R^2$ is required to be protected, and is converted into $R^2$ by deprotection, with the proviso that when a compound does not require the deprotection indicated in Step 4, $R^2$ and $R^5$ are the same substituent groups.]

More specifically, a phenylalanylamide (III) is condensed with epoxysuccinic acid monoethyl ester (II) to obtain a compound (IV). The ester moiety of this compound is hydrolyzed into a compound (V). An amine derivative (VI) is condensed with the compound (V) in the presence of a condensing agent, and deprotection is then conducted as needed, thereby obtaining a compound (I) according to the present invention.

The individual steps will hereinafter be described.

<Step 1>

The compound (II) easily obtained in accordance with the process already known from a literature [Chemical and Pharmaceutical Bulletin, Vol. 35, p. 1098, (1987)] is condensed with the compound (III) in a proper solvent, thereby obtaining the amide derivative (IV). As condensing agents used in this reaction, may be mentioned condensing agents commonly used in organic synthetic reactions. Examples thereof include N,N-dicyclohexylcarbodiimide, 1-ethyl-3-(3-dimethylaminopropyl)carbodiimide hydrochloride, 1,1-carbonyldiimidazole, 2-chloro-1,3-dimethylimidazolinium chloride, ethyl chloroformate, isobutyl chloroformate, pivaloyl chloride, thionyl chloride, phosphorus oxychloride and trifluoroacetic anhydride. This reaction may be conducted via an active ester. Examples of the active ester used at this time include 4-nitrophenyl ester, 1-benzotriazolyl ester and N-hydroxysuccinimide ester. The resultant active ester may or may not be isolated to use. The reaction may also be carried out in the presence of a proper base. Examples of the proper base include organic amines such as pyridine, triethylamine, 2,6-lutidine, N,N-dimethylaminopyridine and diisopropylethylamine. No particular limitation is imposed on the proper solvent so far as it does not affect the reaction. Examples thereof include dichloromethane, chloroform, ethyl acetate, acetonitrile, tetrahydrofuran, dioxane, diethyl ether, diisopropyl ether, benzene, toluene, N,N-dimethylformamide and dimethyl sulfoxide. These solvents may be used either singly or in any combination thereof.

The compound (III) used in Step 1 is synthesized in the following manner.

[wherein $R^6$ represents a protecting group for the amino group, $R^7$ represents a hydrogen atom or an ester residue, and $R^3$ and $R^4$ have the same meanings as defined above.]

More specifically, a phenylalanine derivative (IX) is condensed with an amine compound (X) in a proper solvent to obtain a condensate (XI) (Step 5). $R^6$ is then removed from the condensate to obtain the compound (III) (Step 6). Incidentally, when $R^7$ is a hydrogen atom, the reaction requires a proper condensing agent.

As condensing agents used in the reaction of the compound (IX) with the amine compound (X), may be mentioned condensing agents commonly used in organic synthetic reactions. Examples thereof include N,N-dicyclohexylcarbodiimide, 1-ethyl-3-(3-dimethylaminopropyl)carbodiimide hydrochloride, 1,1-carbonyldiimidazole, 2-chloro-1,3-dimethylimidazolinium chloride, ethyl chloroformate, isobutyl chloroformate, pivaloyl chloride, thionyl chloride, phosphorus oxychloride and trifluoroacetic anhydride.

This reaction may also be carried out in the presence of a proper base. Examples of the proper base include organic amines such as pyridine, triethylamine, 2,6-lutidine, N,N-dimethylaminopyridine and diisopropylethylamine.

When $R^7$ is a p-nitrophenyl group, succinylimide group or 1-benzotriazolyl group, or the like and forms an active ester with the adjacent carboxyl group, the condensate can be obtained by mixing the compound (IX) with the amine compound (X) in a proper solvent without using any condensing agent.

No particular limitation is imposed on the solvent used in this reaction so far as it does not affect the reaction. Examples thereof include dichloromethane, chloroform, ethyl acetate, acetonitrile, tetrahydrofuran, dioxane, diethyl ether, diisopropyl ether, benzene, toluene, N,N-dimethylformamide and dimethyl sulfoxide. These solvents may be used either singly or in any combination thereof.

$R^6$ is removed from the condensate (XI) obtained in Step 5 by an appropriate method, thereby obtaining the amine derivative (III).

The conditions of the reaction depends on $R^6$. When $R^6$ is a $C_{2-5}$ alkyloxycarbonyl group, the deprotection can be carried out by treating the condensate with an acid or base in a proper solvent. No particular limitation is imposed on the proper solvent so far as it does not affect the reaction. Examples thereof include dichloromethane, chloroform, ethyl acetate, tetrahydrofuran, dioxane, diethyl ether, diisopropyl ether, benzene, toluene, N,N-dimethylformamide, dimethyl sulfoxide, acetic acid, methanol, ethanol and water. These solvents may be used either singly or in any combination thereof. Examples of the acid include mineral acids such as hydrochloric acid, hydrobromic acid, sulfuric acid and nitric acid, and organic acids such as trifluoroacetic acid, p-toluene-sulfonic acid and methanesulfonic acid.

Examples of the base include sodium hydroxide, potassium hydroxide, lithium hydroxide and barium hydroxide. This reaction may also be carried out by a combination of a sulfur-containing compound and an acid. Examples of the sulfur-containing compound include thioanisole, dimethyl sulfide and methionine. Examples of the acid include mineral acids such as hydrochloric acid, hydrobromic acid, sulfuric acid and nitric acid, and organic acids such as methanesulfonic acid, p-toluenesulfonic acid and trifluoroacetic acid.

When $R^6$ is a benzyloxycarbonyl group, the object can be achieved by catalytic hydrogenation. Examples of a catalyst used include palladium on carbon, palladium on alumina, palladium black, platinum on carbon, platinum oxide, platinum on alumina and platinum black. The amount of the catalyst used is desirably within a range of from 10% to 200% of the weight of the substrate. Examples of a solvent used include methanol, ethanol, water, acetic acid, tetrahydrofuran, dioxane, diethyl ether, diisopropyl ether, ethyl acetate, dichloromethane and chloroform. These solvents may be used either singly or in any combination thereof.

The amine derivative (III) can also be synthesized via a cyclic N-carboxylic acid anhydride.

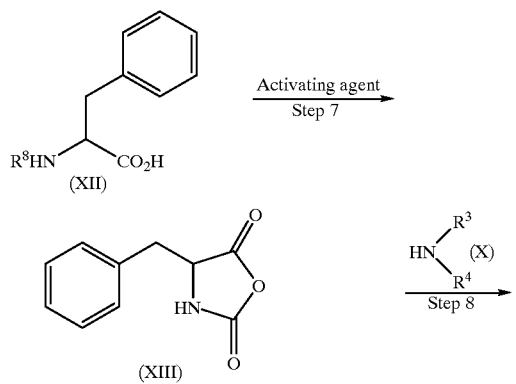

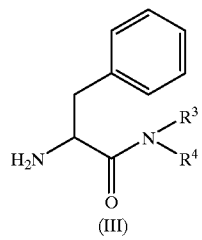

(III)

[wherein $R^8$ represents hydrogen or a carbamate type protecting group for the amino group, and $R^3$ and $R^4$ have the same meaning as defined above.]

A phenylalanine derivative (XII) is treated with an activating agent in a proper solvent, whereby it can be converted into a cyclic N-carboxylic acid anhydride (XIII) (Step 7). Examples of the carbamate type protecting group for the amino group include methoxycarbonyl, ethoxycarbonyl and benzyloxycarbonyl groups, and examples of the activating agent include phosgene, phosgene dimer, triphosgene, phosphorus tribromide, phosphorus trichloride, phosphorous pentachloride and thionyl chloride. No particular limitation is imposed on the solvent used in this reaction so far as it does not affect the reaction. Examples thereof include dichloromethane, chloroform, ethyl acetate, acetonitrile, tetrahydrofuran, dioxane, diethyl ether, diisopropyl ether, benzene, toluene, N,N-dimethylformamide and dimethyl sulfoxide. These solvents may be used either singly or in any combination thereof. The acid anhydride (XIII) may or may not be isolated to use it in the subsequent step.

The N-carboxylic acid anhydride (XIII) obtained in Step 7 is reacted with an amine compound (X) in the presence or absence of a proper solvent, whereby it can be converted into the phenylalanine amide derivative (III) (Step 8). No particular limitation is imposed on the proper solvent so far as it does not affect the reaction. Examples thereof include dichloromethane, chloroform, ethyl acetate, acetonitrile, tetrahydrofuran, dioxane, diethyl ether, diisopropyl ether, benzene, toluene, methanol, ethanol and water. These solvents may be used either singly or in any combination thereof.

<Step 2>

The amide derivative (IV) obtained in Step 1 is hydrolyzed, thereby obtaining the carboxylic acid (V). As a reaction reagent, an inorganic base is used. Preferable examples thereof include lithium hydroxide, sodium hydroxide, potassium hydroxide, calcium hydroxide, barium hydroxide, lithium carbonate, sodium carbonate and potassium carbonate. No particular limitation is imposed on a solvent used so far as it does not affect the reaction. Examples thereof include tetrahydrofuran, dioxane, diethyl ether, isopropyl ether, benzene, toluene, N,N-dimethylformamide, dimethyl sulfoxide, methanol, ethanol, n-propanol, 2-propanol and water. These solvents may be used either singly or in any combination thereof.

<Step 3>

The carboxylic acid (V) obtained in Step 2 is reacted with the amine derivative (VI) in the presence of a condensing agent in a proper solvent, thereby obtaining a condensate (VII). Examples of the solvent used in the reaction include dichloromethane, chloroform, ethyl acetate, acetonitrile, tetrahydrofuran, dioxane, diethyl ether, benzene, toluene, N,N-dimethylformamide and dimethyl sulfoxide. These solvents may be used either singly or in any combination thereof. As the condensing agent, may be mentioned condensing agents commonly used in organic synthetic reactions. Examples thereof include N,N-dicyclohexylcarbodiimide, 1-ethyl-3-(3-dimethylaminopropyl)carbodiimide hydrochloride, 1,1-carbonyldiimidazole, 2-chloro-1,3-dimethylimidazolinium chloride, ethyl chloroformate, isobutyl chloroformate, pivaloyl chloride, thionyl chloride, phosphorus oxychloride and trifluoroacetic anhydride.

This reaction may also be carried out in the presence of a proper base. Examples of the proper base include organic amines such as pyridine, triethylamine, 2,6-lutidine, N,N-dimethylaminopyridine and diisopropylethylamine.

Further, this reaction may be conducted via an active ester. Examples of the active ester used at this time include 4-nitrophenyl ester, 1-benzotriazolyl ester and N-hydroxysuccinimide ester. The resultant active ester may or may not be isolated to use. Incidentally, the compound (VII) can be obtained even when the order of the condensation of the compound (III) and the compound (VI) is changed.

<Step 4>

The condensate (VII) obtained in Step 3 can be subjected to optional deprotection and subsequent functional-group conversion, thereby converting it into the compound (I). As the conditions of the deprotection, the process described in Step 6 may be used. The functional-group conversion subsequent to the deprotection means functional-group conversion such as acylation and can be carried out by reacting the deblocked compound with an acylating agent in the presence of a basic compound in a proper solvent, or with an acid in the presence of a condensing agent. Examples of the proper solvent include the same solvents as those mentioned in Step 1. The basic compound is preferably an organic base. Examples thereof include triethylamine, pyridine, N,N-dimethylaminopyridine, diisopropylethylamine and 1,8-diazabicyclo-[5,4,0]-7-undecene. Examples of the acylating agent include acid anhydrides such as acetic anhydride, propionic anhydride, trifluoroacetic anhydride and benzoic anhydride, and acid chlorides such as acetyl chloride, propionyl chloride, trifluoroacetyl chloride and benzoyl chloride. Examples of the condensing agent include the same agents as those mentioned in Step 3. The acid is preferably an organic acid having 1 to 7 carbon atoms. Examples thereof include formic acid, acetic acid, propionic acid, butyric acid, isobutyric acid, valeric acid, isovaleric acid, pivalic acid, heptanoic acid and benzoic acid.

The intermediates for preparation and invention compounds thus obtained can be purified in accordance with separating means generally used in synthetic chemistry, such as recrystallization, distillation and column chromatography.

As apparent from a pharmacological test, which will be described subsequently, the compounds according to the present invention have an inhibitory activity against cysteine proteases such as cathepsin L, cathepsin B and cathepsin H or the like. More preferably, $IC_{50}$ of the invention compounds against cathepsin L is at most about $\frac{1}{100}$ of the $IC_{50}$ inhibiting cathepsin B, so that the inhibitory selectivity of the invention compounds is specific for cathepsin L. The compounds according to the present invention also strongly inhibit cathepsin K, which is a family enzyme of cathepsin L. In an inhibitory test of pit formation by bone resorption using an ivory slice in accordance with the method described in J. Clin. Invest., 80, 425–429 (1981) and FEBS Letters, 321, 247–250 (1993), the compounds according to the present invention strongly inhibited pit formation at a concentration of from $10^{-9}$ M to $10^{-7}$ M. To a bone resorption model prepared by inoculation of mouse colon cancer colon 26 cells subcutaneously over the calvaria in mice in accordance with the method described in J. Jpn. Soc. Cancer Ther., 28, 1671–1676 (1993), the compounds according to the present invention were administered intraperitoneally, intravenously or orally in a dose of 3 to 50 mg/kg/day for 5 days from the day of the tumor transplantation. As a result, the compounds significantly inhibited bone resorption and without any toxicity. The compounds according to the present invention have excellent in vivo stability and high safety and inhibitory activities against cathepsin L and its family enzymes and against bone resorption. Accordingly, the compounds may be used as agents for preventing and treating diseases caused by cysteine proteases, such as muscular dystrophy, muscular atrophy, myocardial infarction, apoplectic stroke, Alzheimer's disease, disturbance of consciousness and dyskinesis upon head injury, multiple sclerosis, peripheral nerve neuropathy, cataract, inflammation, allergy, fulminant hepatitis, osteoporosis, hypercalcemia, breast cancer, prostatic cancer and prostatic hypertrophy, or agents for inhibiting cancerous proliferation and preventing metastasis and platelet aggregation inhibitors. Especially, the compounds are useful as agents for preventing and treating osteopathy, particularly, agents for treating and preventing metabolic osteopathy such as osteoporosis, hypercalcemia and bone metastasis of cancer because they specifically inhibits cathepsin L and its family enzymes to inhibit bone resorption.

When the invention compounds and the salts thereof are applied to treatment for the above-described diseases, including osteoporosis, of mammals including the human, they are orally or parenterally administered. The dose thereof varies depending on the age, sex, weight and condition of a patient to be administered. However, they are orally or parenterally administered in a dose of generally 0.1 to 1,000 mg, preferably 1 to 1,000 mg, more preferably 5 to 500 mg, per day for an adult. Meanwhile, the administration may be divided into 2 to 3 times per day, or may be once per day.

The invention compounds can be orally or parenterally administered in the form of a solid preparation such as tablets, capsules, granules or powder, or a liquid preparation such as syrup or injection by blending an effective amount of the invention compound with pharmaceutically acceptable carriers.

As the pharmaceutically acceptable carriers, there may be used various kinds of organic or inorganic carriers commonly used as preparation materials. They are incorporated as excipients, lubricants, binders and disintegrators for solid preparations, or as solvents, solubilizing agents, suspending agents, isotonicity agents, buffers and analgesics for liquid preparations. Additives for preparations, such as antiseptics, antioxidants, colorants and sweetners may also be used as needed. Suitable examples of the excipients include lactose, D-mannitol, starch, crystalline cellulose and precipitated anhydrous silicic acid. Suitable examples of the lubricants include magnesium stearate, calcium stearate, talc and colloidal silica. Suitable examples of the binders include crystalline cellulose, sucrose, D-mannitol, dextrin, hydroxypropyl cellulose, hydroxypropylmethyl cellulose and polyvinyl pyrrolidone. Suitable examples of the disintegrators include starch, carboxymethyl cellulose, calcium carboxymethyl cellulose, sodium crosscalmelol and sodium carboxymethyl starch.

Suitable examples of the solvents include water for injections, alcohol, propylene glycol, macrogol, sesame oil and corn oil. Suitable examples of the solubilizing agents include polyethylene glycol, propylene glycol, D-mannitol, benzyl benzoate, ethanol, trisaminomethane, cholesterol, triethanolamine, sodium carbonate and sodium citrate. Suitable examples of the suspending agents include surfactants such as triethanolamine stearate, sodium lauryl sulfate, laurylaminopropionic acid, lecithin, benzalkonium chloride, benzethonium chloride and glycerol monostearate, and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Suitable examples of the buffers include phosphates, acetates, carbonates and citrates. Suitable examples of the analgesics include benzyl alcohol. Suitable examples of the antiseptics include p-hydroxybenzoic acid esters, chlorobutanol, benzyl alcohol, phenethyl alcohol, dehydroacetic acids and sorbic acid. Suitable examples of the antioxidants include sulfites and ascorbates.

EXAMPLES

The present invention will hereinafter be described in detail by the following Examples. However, the present invention is not limited to these Examples.

Preparation Example 1
L-Phenylalanine dimethylamide hydrochloride:

A 50% aqueous solution (1.0 ml, 11.11 mmol) of dimethylamine was added to an ethyl acetate solution (50 ml) of N-t-butoxycarbonyl-L-phenylalanine 4-nitrophenyl ester (3.0 g, 7.77 mmol). The mixture was stirred at room temperature for 9 hours. After completion of the reaction, the reaction mixture was washed with a dilute aqueous solution of sodium hydroxide until washings became free from coloring, and then washed with water and saturated brine, and was dried over anhydrous magnesium sulfate. The solvent was distilled off under reduced pressure, and the resultant residue was subjected to deprotection with a 4N solution of hydrochloric acid/ethyl acetate to obtain 1.5 g of the title compound.

mp: 216–217° C.; $^1$H-NMR (DMSO-$d_6$) δ: 2.60(3H,s), 2.79(3H,s), 2.90(1H,dd,J=8.2,13.4 Hz), 3.10(1H,dd,J=6.1, 13.4 Hz), 4.53(1H,br.t,J=7.1 Hz), 7.20–7.34(5H,m). Mass (FAB(+)) m/e: 193 (MH)$^+$.

Preparation Example 2
L-3-trans-[(S)-1-Dimethylcarbamoyl-2-phenylethylcarbamoyl]oxirane-2-carboxylic acid:

Triethylamine (7.7 ml, 55.0 mmol) was added to a tetrahydrofuran solution (160 ml) of ethyl 4-nitrophenyl L-trans-epoxysuccinate (14.0 g, 49.8 mmol) and the compound (12.0 g, 52.3 mmol) obtained in Preparation Example 1. The mixture was stirred at room temperature for 2.5 hours. Solids deposited were separated by filtration, and the filtrate was subjected to column chromatography on silica gel (isopropyl ether:chloroform=3:1—methanol:chloroform=1:10). The thus-obtained condensate was dissolved in ethanol (100 ml), to which potassium hydroxide (3.1 g, 55.6 mmol)/water (3 ml) were added under cooling with ice water. The resultant mixture was stirred for 3.5 hours as it was. After the solvent was distilled off under reduced pressure, a small amount of water was added to the residue. The resultant mixture was washed with tetrahydrofuran-ethyl acetate. An aqueous phase was acidified with 1N hydrochloric acid, and extracted 3 times with ethyl acetate. After the resultant extract was dried over anhydrous magnesium sulfate, the solvent was distilled off under reduced pressure to obtain 12.0 g of the title compound (foam).

$^1$H-NMR (DMSO-$d_6$) δ: 2.79(3H,s), 2.80–2.86(1H,m), 2.87(3H,s), 2.95(1H,dd,J=6.1,13.2 Hz), 3.38(1H,d,J=1.7 Hz), 3.62(1H,d,J=1.7 Hz), 4.93(1H,dt,J=6.4,14.6 Hz), 7.20–7.30(5H,m), 8.80(1H,d,J=8.3 Hz), 13.38(1H,br.s). Mass (FAB(–)) m/e: 305 (M–H)$^-$.

Preparation Example 3
L-Phenylalanine propylamide hydrochloride:

Following a process similar to the process of Preparation Example 1, a condensate was obtained from N-t-butoxycarbonyl-L-phenylalanine (15.0 g, 56.5 mmol) and n-propylamine (3.5 g, 58.4 mmol). This condensate (6.0 g) was subjected to deprotection to obtain 4.7 g of the title compound.

mp: 154–155° C.; $^1$H-NMR (DMSO-$d_6$) δ: 0.74(3H,t,J=11.2 Hz), 1.26–1.38(2H,m), 2.86–2.97(1H,m), 2.98–3.13 (3H,m), 3.95(1H,t,J=6.4 Hz), 7.20–7.40(5H,m), 8.32(2H, br.s), 8.44(1H,t,J=5.6 Hz). Mass (FAB(+)) m/e: 207 (MH)$^+$.

Preparation Example 4
L-3-trans-[(S)-1-Propylcarbamoyl-2-phenylethylcarbamoyl]oxirane-2-carboxylic acid:

Following a process similar to the process of Preparation Example 2, the title compound (1.8 g) was obtained from the compound (2.0 g, 8.2 mmol) obtained in Preparation Example 3.

mp: 184–186° C.; $^1$H-NMR (DMSO-$d_6$) δ: 0.79(3H,t,J=7.3 Hz), 1.31–1.41(2H,m), 2.80(1H,dd,J=9.5,13.6 Hz), 2.92–3.08(3H,m), 3.29(1H,d,J=1.7 Hz), 3.59(1H,d,J=1.7 Hz), 4.48–4.55(1H,m), 7.17–7.30(5H,m), 8.06(1H,t,J=5.6 Hz), 8.58(1H,d,J=8.6 Hz). Mass (FAB(+)) m/e: 321 (MH)$^+$.

Preparation Example 5
L-Phenylalanine-2-phenylethylamide hydrochloride:

2-Phenylethylamine (577 mg, 4.8 mmol) was added to an ethyl acetate solution (50 ml) of N-benzyloxycarbonyl-L-phenylalanine 4-nitrophenyl ester (2.0 g, 4.8 mmol). The mixture was stirred at room temperature for 9 hours. After completion of the reaction, the reaction mixture was washed with a dilute aqueous solution of sodium hydroxide until washings became free from coloring, and then washed with water and saturated brine, and was dried over anhydrous magnesium sulfate. The solvent was distilled off under reduced pressure to obtain 1.9 g of a condensate. The thus-obtained condensate (1.65 g, 4.3 mmol) was dissolved in a mixed solvent (100:1) of methanol-chloroform, and 10% palladium on carbon (1.65 g) was added to the solution. The mixture was stirred at room temperature for 1 hour in a hydrogen atmosphere. After completion of the reaction, the catalyst was separated by filtration, and the filtrate was concentrated under reduced pressure to obtain 1.13 g of the title compound.

mp: 64–67° C.; $^1$H-NMR (DMSO-$d_6$) δ: 1.91(2H,br.s), 2.58(1H,dd,J=8.2,13.3 Hz), 2.66(2H,t,J=7.3 Hz), 2.88(1H, dd,J=5.1,13.3 Hz), 3.25–3.41(1H,m), 7.15–7.28(10H,m), 7.90(1H,br.t,J=6.0 Hz). Mass (FAB(+)) m/e: 269 (MH)$^+$.

Preparation Example 6
L-3-trans-[(S)-1-(2-Phenylethylcarbamoyl)-2-phenylethylcarbamoyl]oxirane-2-carboxylic acid:

Following a process similar to the process of Preparation Example 2, the title compound (1.10 g) was obtained from the compound (1.0 g, 3.90 mmol) obtained in Preparation Example 5.

mp: 154–155.5° C.; $^1$H-NMR (DMSO-$d_6$) δ:
2.67(2H,t,J=7.3 Hz), 2.75(1H,dd,J=9.8,13.2 Hz), 2.94 (1H,dd,J=4.9,13.7 Hz), 3.21–3.28(2H,m), 3.29(1H,d,J=2.0 Hz), 3.58(1H,d,J=1.3 Hz), 4.47–4.52(1H,m), 7.18–7.30 (10H,m), 8.25(1H,br.t,J=5.4 Hz), 8.66(1H,d,J=8.8 Hz). Mass (FAB(+)) m/e: 381 (MH)$^+$.

Preparation Example 7
2-(t-Butoxycarbonylaminomethyl)aniline:

2-Aminobenzylamine (5.0 g, 40.9 mmol) and triethylamine (4.1 g, 40.9 mmol) were dissolved in a mixed solvent (50 ml) of dioxane-water (2:1). A dioxane solution (8.9 g/10 ml) of di-t-butyl carbonate was added dropwise to the solution under cooling with ice water. The mixture was stirred for 2 hours as it was. After the reaction mixture was diluted with ethyl acetate, an aqueous phase was removed, and an organic phase was washed 3 times with water and once with saturated brine, and dried over anhydrous magnesium sulfate. The solvent was distilled off under reduced pressure, and the residue was crystallized from diisopropyl ether-hexane to obtain 6.70 g of the title compound.

mp: 94–95° C.; $^1$H-NMR (DMSO-$d_6$) δ: 1.38(9H,s), 3.94(2H,d,J=6.1 Hz), 4.97(2H,s), 6.48(1H,dd,J=6.5,6.5 Hz), 6.58(1H,d,J=7.3 Hz), 6.91(1H,d,J=7.1 Hz), 6.92(1H,dd,J=6.8,6.8 Hz), 7.22(1H,br.t,J=6.1 Hz). Mass (EI(+)) m/e: 222 (M)$^+$.

Preparation Example 8
3-(t-Butoxycarbonylaminomethyl)aniline:

Sodium azide (10.0 g, 153.8 mmol) was added to an N,N-dimethylformamide solution (100 ml) of 3-nitrobenzyl bromide (5.0 g, 23.14 mmol). The mixture was stirred at room temperature for 5 hours. After the reaction mixture was diluted with ethyl acetate, washed 5 times with water and once with saturated brine, and then dried over anhydrous magnesium sulfate. The solvent was distilled off under reduced pressure, and the residue was subjected to column chromatography on silica gel (hexane:ethyl acetate=5:1) to obtain the intended azide compound. This azide compound was dissolved in dioxane (100 ml), and 10% palladium on carbon (500 mg) was added to the solution. The mixture was stirred at room temperature for 4 hours in a hydrogen atmosphere. After completion of the reaction, the catalyst was separated by filtration, and water (50 ml) and triethylamine (2.8 ml, 20.0 mmol) were added to the filtrate. A dioxane solution (10 ml) of di-t-butyl carbonate (4.4 g, 20 mmol) was further added dropwise to the filtrate under cooling with ice water. The mixture was stirred for 24 hours as it was. After the reaction mixture was diluted with ethyl acetate, it was washed with a saturated solution of sodium hydrogencarbonate and then with saturated brine and dried over anhydrous magnesium sulfate. The solvent was distilled off under reduced pressure, and the residue was subjected to column chromatography on silica gel (hexane:ethyl acetate=2:1) to obtain 652 mg of the title compound (oil).

$^1$H-NMR (DMSO-$d_6$) δ: 1.38(9H,s), 3.95(2H,d,J=6.1 Hz), 4.98(2H,s), 6.39–6.41(3H,m), 6.90(1H,dd,J=7.6,7.6 Hz), 8.38(1H,s). Mass (EI(+)) m/e: 222 (M)$^+$.

Preparation Example 9
4-(t-Butoxycarbonylaminomethyl)aniline:

Following a process similar to the process of Preparation Example 7, the title compound (7.2 g) was obtained from 4-(aminomethyl)aniline (5.0 g, 40.9 mmol).

mp: 88–90° C.; $^1$H-NMR (DMSO-$d_6$) δ: 1.36(9H,s), 3.91(2H,d,J=6.1 Hz), 4.90(2H,s), 6.47(1H,d,J=8.3 Hz), 6.87 (1H,d,J=8.3 Hz), 7.12(1H,br.t,J=5.8 Hz). Mass (EI(+)) m/e: 222 (M)$^+$.

Preparation Example 10
N-t-Butoxycarbonyl-N'-phenylethylenediamine:

Following a process similar to the process of Preparation Example 7, the title compound (2.1 g) was obtained from N-phenylethylenediamine (2.0 g, 14.7 mmol).

mp: 84–85° C.; $^1$H-NMR (DMSO-$d_6$) δ: 1.37(9H,s), 3.02–3.08(4H,m), 5.54(1H,br.t,J=5.1 Hz), 6.50(1H,dd,J=7.3,7.3 Hz), 6.54(2H,d,J=7.8 Hz), 6.87(1H,br.t,J=5.6 Hz), 7.05(2H,dd,J=7.3,8.3 Hz). Mass (FAB(+)) m/e: 381 (MH)$^+$.

Preparation Example 11
N-Benzenesulfonylethylenediamine:

N-Benzyloxycarbonylethylenediamine hydrochloride (2.3 g, 10.0 mmol) obtained in accordance with the process described in Hoppe-Seyler's, Z. Physiol. Chem., 349, 251 (1968) and benzenesulfonyl chloride (1.2 ml, 0.95 mmol) were suspended in water (100 ml). After triethylarine (1.4 ml) was added to the suspension, a 1N aqueous solution (10 ml) of sodium hydroxide was gradually added over about 10 minutes, and the mixture was stirred at 70° C. for 30 minutes. Toluene was added to the reaction mixture, and the solvent was distilled off under reduced pressure. The resultant condensate was dissolved in methanol, and 10% palladium on carbon (1.3 g) was added to the solution. The mixture was stirred f or 3 hours in a hydrogen atmosphere. The catalyst was separated by filtration, and the solvent was distilled off under reduced pressure to obtain 727 mg of the title compound (oil).

$^1$H-NMR (CDCl$_3$) δ: 2.77–2.85(2H,m), 2.95–3.03(2H, m), 7.49–7.70(3H,m), 7.85–8.00(2H, m). Mass (FAB(+)) m/e: 201 (MH)$^+$.

Preparation Example 12
2-t-Butoxycarbonylamino-4-(2-hydroxyethyl) thiazole:

Ethyl 2-amino-4-thiazole-acetate (5.0 g, 26.8 mmol) and triethylamine (3.8 ml, 26.8 mmol) were dissolved in a dichloromethane (20 ml). Di-t-butyl carbonate (7.0 g, 32.2 mmol) was added to the solution under cooling with ice water. The mixture was stirred overnight at room temperature. After 18 hours, additional di-t-butyl carbonate (1.4 g, 13.4 mmol) was added, and the resultant mixture was stirred at room temperature for 6 hours. After completion of the reaction, the solvent was distilled off under reduced pressure, and the resultant residue was dissolved in ethyl acetate, washed with water and saturated brine, and then dried over anhydrous magnesium sulfate. After the solvent was distilled off under reduced pressure, the residue was subjected to column chromatography on silica gel (hexane:ethyl acetate=3:1) to obtain 3.1 g of ethyl 2-t-butoxycarbonylamino-4-thiazole-acetate. A part (2.0 g, 7.0 mmol) of this compound was dissolved in a mixed solvent of ethanoltetrahydrofuran (3:2, 50 ml). Lithium chloride (592 mg, 14.0 mmol) and sodium borohydride (528 mg, 14.0 mmol) were added to the solution at room temperature, and the mixture was stirred at room temperature for 6 hours. After 6 hours, sodium borohydride (530 mg, 14.1 mmol) and lithium chloride (592 mg, 14.0 mmol) were additionally added, and the resultant mixture was stirred further for 3 hours at room temperature. The reaction mixture was diluted with ethyl acetate, washed with water, diluted hydrochloric acid, a saturated aqueous solution of sodium hydrogencarbonate, water and saturated brine in that order, and dried over anhydrous magnesium sulfate. The solvent was distilled off under reduced pressure, and the residue was subjected to column chromatography on silica gel (hexane:ethyl acetate=1:1 to 2:3) to obtain 959 mg of the title compound (oil).

$^1$H-NMR (DMSO-$d_6$) δ: 1.46(9H,s), 2.68(2H,t,J=6.8 Hz), 3.62(2H,dd,J=7.1,12.4 Hz), 4.58(1H,t,J=5.4 Hz), 6.71(1H, s), 11.30(1H,br.s). Mass (FAB(+)) m/e: 245 (MH)$^+$.

Preparation Example 13
2-t-Butoxycarbonylamino-4-(2-aminoethyl)thiazole:

The compound (949 mg, 3.88 mmol) obtained in Preparation Example 12 was dissolved in a dichloromethane (50 ml), and triethylamine (432 mg, 4.27 mmol) and 4-chlorobenzenesulfonyl chloride (982 mg, 4.66 mmol) were added to the solution under cooling with ice water. The mixture was stirred at room temperature. After 3 hours, N,N-dimethylaminopyridine (47 mg, 0.39 mmol) was added, and the resultant mixture was stirred as it was. After 3.5 hours, 4-chlorobenzenesulfonyl chloride (491 mg, 2.33 mmol) was added, and 23 hours and 45 minutes after that, 4-chlorobenzenesulfonyl chloride (819 mg, 3.88 mmol) and triethylamine (393 mg, 3.88 mmol) were added. The resultant mixture was stirred for 5 days. After the solvent was distilled off under reduced pressure, ethyl acetate was added to the residue, and the resultant mixture was washed with water, diluted hydrochloric acid, water, a saturated aqueous solution of sodium hydrogencarbonate and saturated brine in that order and dried over anhydrous sodium sulfate. After the solvent was distilled off under reduced pressure, the residue was subjected to column chromatography on silica gel (hexane:ethyl acetate=3:1 to 1:1) to obtain 1.18 g of an sulfone derivative. A part (1.15 g, 2.75 mmol) of this compound was dissolved in N,N- dimethylformamide (30 ml). Sodium azide (1.78 g, 27.45 mmol) was added to the solution, and the mixture was stirred at 60° C. for 3 hours. After cooling the reaction mixture down to room temperature, it was diluted with ethyl acetate, washed several times with water and once with saturated brine, and dried over anhydrous magnesium sulfate. The solvent was distilled off under reduced pressure, and the residue was subjected to column chromatography on silica gel (hexane:ethyl acetate=2:1) to obtain 739 mg of an azide compound. A part (730 mg, 2.71 mmol) of this azide compound was dissolved in ethanol (50 ml), and 10% palladium on carbon (146 mg) was added to the solution. The mixture was stirred for 1.5 hours in a hydrogen atmosphere. After the catalyst was separated by filtration, the filtrate was concentrated under reduced pressure to obtain 652 mg of the title compound (oil).

$^1$H-NMR (DMSO-$d_6$) δ: 1.45(9H,s), 2.59(2H,t,J=7.1 Hz), 2.77(2H,t,J=6.8 Hz), 4.73(2H,br.s), 6.68(1H,s). Mass (FAB (+)) m/e: 244 (MH)$^+$.

Preparation Example 14
Benzyl 4-aminobenzoate hydrochloride:

4-Aminobenzoic acid (5.0 g, 36.46 mmol) was dissolved in a mixed solvent of 1,4-dioxane/1N sodium hydroxide (1/1, 50 ml), and a 1,4-dioxane solution (9.5 g, 43.75 mmol/25 ml) of di-t-butyl carbonate was added dropwise to the solution under cooling with ice water. The mixture was stirred at room temperature. After 7.5 hours, additional di-t-butyl carbonate (1.5 g) was added to continue stirring. After 24 hours, 6N hydrochloric acid was added to the reaction mixture to acidify it, and the solvent was then distilled off under reduced pressure. The resultant residue was dissolved in ethyl acetate, and the solution was washed 4 times with water and once with saturated brine and dried over anhydrous magnesium sulfate. The solvent was distilled off under reduced pressure to obtain 9.28 g (39.10 mmol) of 4-butoxycarbonylaminobenzoic acid as a crude product. This compound was dissolved together with benzyl alcohol (4.23 g, 39.10 mmol) and N,N-dimethylaminopyridine (478 mg, 3.91 mmol) in N,N-dimethylformamide (100 ml), and 1-ethyl-3-(3-dimethylaminopropyl)carbodiimide hydrochloride (8.99 g, 46.92 mmol) was added to the solution under cooling with ice water. The mixture was stirred at room temperature for 8 hours. The reaction mixture was diluted with ethyl acetate, washed with water (twice), a 10% aqueous solution of citric acid, a saturated aqueous solution of sodium hydrogencarbonate and saturated brine, and dried over anhydrous magnesium sulfate. The solvent was distilled off under reduced pressure, and the residue was subjected to column chromatography on silica gel (toluene:ethyl acetate=20:1) to obtain 4.09 g (12.5 mmol) of a benzyl ester. The thus-obtained ester was dissolved in ethyl acetate (70 ml), and 4N hydrochloric acid/ethyl acetate (70 ml) was added to the solution. The mixture was stirred at room temperature. After 1.5 hours, additional 4N hydrochloric acid/ethyl acetate (70 ml) was added to continue stirring. After 1 hour, the reaction was stopped, and solids deposited were collected by filtration. The thus-obtained solids were suspended in ethyl acetate, and the suspension was ultrasonically washed and then filtered to obtain 2.86 g of the title compound.

mp: 108–110° C.; $^1$H-NMR (DMSO-$d_6$) δ: 5.27(2H,s), 6.81(2H,d,J=8.3 Hz), 7.32–7.45(5H,m), 7.78(2H,d,J=8.8 Hz), 8.56(2H,br.s). Mass (FAB(+)) m/e: 228 (MH)$^+$.

Preparation Example 15
N-Methyl-4-ethylaniline:

4-Ethylaniline (2.4 g, 20 mmol) was dissolved in dichloromethane (150 ml), and triethylamine (8.4 ml, 60 mmol) and ethyl chloroformate (5.8 ml, 60 mmol) were added to the solution to stir the mixture for 2 hours. The reaction mixture was diluted with ethyl acetate, washed with a saturated aqueous solution of sodium hydrogencarbonate and saturated brine and then dried over anhydrous magnesium sulfate. The solvent was distilled off under reduced pressure, and the residue was dissolved in diethyl ether (20 ml). The solution was added dropwise to a suspension (20 ml) of lithium aluminum hydride (2.4 g, 63.2 mmol) in diethyl ether under cooling with ice water in a nitrogen atmosphere. The mixture was stirred for 1 hours as it was, and for 2 hours at room temperature. The solvent was distilled off under reduced pressure, and tetrahydrofuran (20 ml) was added to the residue. The resultant mixture was heated under reflux for 1 hour and 40 minutes. Ice and then water were gradually added to the reaction mixture. After potassium sulfate was additionally added, the mixture was extracted with ethyl acetate. The extract was additionally extracted with 1N hydrochloric acid. After the resultant extract was basified with a 4N aqueous solution of sodium hydroxide, it was extracted 3 times in total with ethyl acetate (twice) and diethyl ether (once), and then dried over anhydrous magnesium sulfate. The solvent was distilled off under reduced pressure, and the residue was subjected to column chromatography on silica gel (hexane:ethyl acetate=20:1) to obtain 1.8 g of the title compound (oil).

$^1$H-NMR (DMSO-$d_6$) δ: 1.10(3H,t,J=7.6 Hz), 2.44(2H,q, J=7.6 Hz), 2.63(3H,d,J=5.4 Hz), 6.45(2H,d,J=8.3 Hz), 6.91 (2H,d,J=8.3 Hz). Mass (EI(+)) m/e: 135 (M)$^+$.

Preparation Example 16
D-3-trans-[(S)-1-Dimethylcarbamoyl-2-phenylethylcarbamoyl]oxirane-2-carboxylic acid:

Monoethyl D-trans-epoxysuccinate (3.0 g, 18.7 mmol), 1-ethyl-3-(3-dimethylaminopropyl)carbodiimide hydrochloride (3.95 g, 21.0 mmol) and 1-hydroxybenzotriazole (2.8 g, 21.0 mmol) were dissolved in N,N-dimethylformamide (50 ml), and the compound (5.6 g, 24.4 mmol) prepared in Preparation Example 1 was added to the solution. Triethylamine (2.9 ml, 21 mmol) was added dropwise to the mixture. After the reaction mixture was stirred at room temperature for 2 hours, it was poured into water to conduct extraction twice with ethyl acetate. The extracts were collected, washed with a saturated aqueous solution of sodium hydrogencarbonate, saturated brine, 1N hydrochloric acid and saturated brine in that order, and dried over anhydrous magnesium sulfate. After the solvent was distilled off under reduced pressure, the resultant residue was subjected to column chromatography on silica gel (hexane:ethyl acetate=1:2) to obtain 2.75 g of the intended condensate. The condensate was hydrolyzed in accordance with the same process as described in Preparation Example 2 to obtain 2.43 g of the title compound.

$^1$H-NMR (DMSO-$d_6$) δ: 2.79(3H,s), 2.75–2.90(1H,m), 2.85(3H,s), 2.95(1H,dd,J=6.6,13.2 Hz), 3.27–3.35(1H,m), 3.63(1H,d,J=1.7 Hz), 4.86–4.96(1H,m), 7.17–7.31(5H,m), 8.88(1H,d,J=8.1 Hz). Mass (FAB(+)) m/e: 307 (MH)$^+$.

Preparation Example 17

N-t-butoxycarbonyl-L-phenylalanine methylamide:

N-t-Butoxycarbonyl-L-phenylalanine (2.65 g, 10.0 mmol) was dissolved in N,N-dimethylformamide (20 ml). To the solution were added a 40% aqueous solution (0.8 ml, 10.3 mmol) of methylamine, 1-hydroxybenzotriazole (1.48 g, 11.0 mmol) and 1-ethyl-3-(3-dimethylaminopropyl)carbodiimide hydrochloride (2.30 g, 12.0 mmol) under cooling with ice water. The mixture was stirred at room temperature for 2.5 hours. The reaction mixture was diluted with ethyl acetate, washed twice with water and each once with a 10% aqueous solution of citric acid, a saturated aqueous solution of sodium hydrogencarbonate and saturated brine, and dried over anhydrous magnesium sulfate. After the desiccant was separated by filtration, the solvent was distilled off under reduced pressure. The resultant solids were washed with diisopropyl ether to obtain 2.41 g of the title compound.

mp: 143.5–145° C.; $^1$ H-NMR (DMSO-$d_6$) δ: 1.30(9H,s), 2.57(3H,d,J=4.6 Hz), 2.71(1H,dd,J=10.2,13.7 Hz), 2.91(1H,dd,J=4.6,13.7 Hz), 4.09(1H,ddd,J=4.6,9.5,9.5 Hz), 6.89(1H,d,J=8.6 Hz), 7.12–7.28(5H,m), 7.83(1H,br.d,J=4.6 Hz). Mass (FAB(+)) m/e: 279 (MH)$^+$.

Preparation Example 18

L-Phenylalanine methylamide hydrochloride:

The compound (2.40 g, 8.62 mmol) obtained in Preparation Example 17 was dissolved in a 4N hydrochloric acid/ethyl acetate solution. The solution was stirred at room temperature for 30 minutes. Solids deposited were collected by filtration and washed with ethyl acetate to obtain 1.62 g of the title compound.

mp: 205–208° C.; $^1$H-NMR (DMSO-$d_6$) δ: 2.58(3H,d,J=4.6 Hz), 3.01–3.07(2H,m), 3.93(1H,br.s), 7.22–7.35(5H,m), 8.32(2H,br.s), 8.46(1H,br.s). Mass (FAB(+)) m/e: 179 (MH)$^+$.

Preparation Example 19

Ethyl L-3-trans-[(S)-1-methylcarbamoyl-2-phenylethylcarbamoyl]oxirane-2-carboxylate:

The compound (1.50 g, 6.99 mmol) obtained in Preparation Example 18 and ethyl L-trans-epoxysuccinate (1.12 g, 6.99 mmol) were dissolved in N,N-dimethylformamide (20 ml), and triethylamine (974 μl, 6.99 mmol), 1-hydroxybenzotriazole (1.04 g, 7.69 mmol), 1-ethyl-3-(3-dimethylaminopropyl)carbodiimide hydrochloride (1.61 g, 8.39 mmol) were added to the solution under cooling with ice water. The mixture was stirred at room temperature for 2 hours. The reaction mixture was diluted with ethyl acetate, washed twice with water and each once with a 10% aqueous solution of citric acid, a saturated aqueous solution of sodium hydrogencarbonate and saturated brine, and dried over anhydrous magnesium sulfate. After the desiccant was separated by filtration, the filtrate was concentrated under reduced pressure. The resultant solids were washed with diisopropyl ether to obtain 1.88 g of the title compound.

mp: 184.5–186.5° C.; $^1$H-NMR (DMSO-$d_6$) δ: 1.21(3H, t,J=7.1 Hz), 2.58(3H,d,J=4.6 Hz), 2.78(1H,dd,J=10.0,13.7 Hz), 3.02(1H,dd,J=4.6,13.7 Hz), 3.41(1H,d,J=1.9 Hz), 3.62 (1H,dd,J=1.7 Hz), 4.14–4.20(2H,m), 4.47(1H,ddd,J=5.2,9.3, 9.3 Hz), 7.18–7.30(5H,m), 8.05(1H,br.d,J=4.6 Hz), 8.68(1H, d,J=8.6 Hz). Mass (FAB(+)) m/e: 321 (MH)$^+$.

Preparation Example 20

L-3-trans-[(S)-1-methylcarbamoyl-2-phenylethylcarbamoyl]oxirane-2-carboxylic acid:

The compound (1.86 g, 5.81 mmol) obtained in Preparation Example 19 was dissolved in ethanol (10 ml), and a 1N aqueous solution (6.1 ml) of sodium hydroxide was added dropwise to the solution under cooling with ice water. The mixture was stirred at room temperature for 20 minutes. The reaction mixture was diluted with water and extracted twice with ethyl acetate. An aqueous phase was then acidified with 1N hydrochloric acid and extracted twice with ethyl acetate. The extract was washed twice with saturated brine and dried over anhydrous magnesium sulfate. After the desiccant was separated by filtration, the solvent was distilled off to obtain 1.39 g of the title compound.

mp: 193–196° C.; $^1$H-NMR (DMSO-$d_6$) δ: 1.17(3H,t,J= 7.1 Hz), 2.58(3H,d,J=4.6 Hz), 2.79(1H,dd,J=10.0,13.7 Hz), 3.02(1H,dd,J=4.9,13.6 Hz), 3.28(1H,d,J=2.0 Hz), 3.57(1H, d,J=1.7 Hz), 4.47(1H,ddd,J=4.9,8.5,10.0 Hz), 7.18–7.29 (5H,m), 8.04(1H,d,J=11.7 Hz), 8.63(1H,d,J=8.5 Hz). Mass (FAB(+)) m/e: 293 (MH)$^+$.

Preparation Example 21

N-{L-3-trans-[(4-Nitrophenoxy)carbonyl]oxirane-2-carbonyl}-L-phenylalanine dimethylamide:

An ethyl acetate solution (20 ml) of N,N-dicyclohexylcarbodiimide (10.1 g, 49 mmol) was added dropwise to an ethyl acetate solution (50 ml) of the compound (15.0 g, 49 mmol) obtained in Preparation Example 2 under cooling with ice water. After 30 minutes, an ethyl acetate solution (20 ml) of 4-nitrophenol (6.8 g, 49 mmol) was added, and the mixture was stirred for 2.5 hours. After the insoluble matter was removed by filtration, the solvent was distilled off, and the residue was subjected to column chromatography on silica gel (hexane:ethyl acetate=1:1 to 1:2) to obtain 13.5 g of the title compound (foam).

$^1$H-NMR (DMSO-$d_6$) δ: 2.80(3H,s), 2.85(1H,dd,J=8.3, 13.4 Hz), 2.88(3H,s), 2.98(1H,dd,J=6.4,13.4 Hz), 3.85(1H, s), 3.93(1H,s), 4.97(1H,ddd,J=6.4,8.0,8.3 Hz), 7.19–7.34 (5H,m), 7.54(2H,d,J=8.3 Hz), 8.34(2H,d,J=8.3 Hz), 8.93 (1H,d,J=8.0 Hz). Mass (FAB(+)) m/e: 428 (MH)$^+$.

Preparation Example 22

1-(2-Cyanoethyl)-4-nitroimidazole:

4-Nitroimidazole (6.87 g, 60 mmol), triethylamine (18.2 g, 180 mmol) and acrylonitrile (9.55 g, 180 mmol) were dissolved in N,N-dimethylformamide (100 ml), and the solution was stirred at 100° C. for 5 hours. The reaction mixture was concentrated under reduced pressure, and chloroform was added to the concentrate. Solids deposited were collected by filtration and dried to obtain 9.2 g of the title compound.

mp: 112–113° C.; $^1$H-NMR (DMSO-$d_6$) δ: 7.94(1H,d,J= 1.2 Hz), 8.52(1H,d,J=1.2 Hz), 3.20(2H,t,J=7.2 Hz), 4.46 (2H,t,J=7.2 Hz). Mass (FAB(+)) m/e: 167 (MH)$^+$.

Preparation Example 23
1-(2-Cyanoethyl)-4-aminoimidazole:

1-(2-Cyanoethyl)-4-nitroimidazole (3.32 g, 20 mmol) was dissolved in methanol (100 ml), and platinum oxide (50 mg) was added to the solution. The mixture was stirred for 12 hours in a hydrogen atmosphere. The catalyst was removed by filtration through Celite, and the filtrate was concentrated under reduced pressure. The residue was subjected to column chromatography on silica gel (chloroform:methanol= 10:1 to 5:1) to obtain 2.31 g of the title compound (oil).

$^1$H-NMR (DMSO-$d_6$) δ: 2.94(2H,t,J=7.9 Hz), 4.11(2H,t, J=7.9 Hz), 6.22(1H,s), 7.19(1H,s). Mass (FAB(+)) m/e: 137 (MH)$^+$.

Preparation Example 24
1-(3-Aminopropyl)-4-aminoimidazole:

1-(2-Cyanoethyl)-4-aminoimidazole (1 g, 6 mmol) was suspended in 3% ammonia/ethanol (50 ml), and Raney nickel was added to the solution. The mixture was stirred at 80° C. for 5 hours in a hydrogen atmosphere. The catalyst was removed by filtration through Celite, and the filtrate was concentrated under reduced pressure. The residue was subjected to column chromatography on silica gel (chloroform:methanol:aqueous ammonia=5:1:0.5) to obtain 620 mg of the title compound (oil).

$^1$H-NMR (DMSO-$d_6$) δ: 1.85(2H,s), 1.92(2H,quintet,J= 6.6 Hz), 2.51(2H,t,J=6.6 Hz), 4.00(2H,t,J=6.6 Hz), 4.82(2H, s), 6.21(1H,s), 7.19(1H,s). Mass (FAB(+)) m/e: 141 (MH)$^+$.

Preparation Example 25
5-Amino-2-(2-aminoethyl)pyridine:

Tin chloride dihydrate (11.65 g, 51.6 mmol) was added to a concentrated hydrochloric acid/ethanol solution (1/1, 32 ml) of 5-nitropyridylacetonitrile (2.55 g, 15.9 mmol) obtained in accordance with the process described in Synthesis, p. 314 (1989) under cooling with ice water. The mixture was stirred at room temperature for 2 hours. After ethanol was distilled off under reduced pressure, the reside was diluted with ethyl acetate, washed with an aqueous solution of sodium carbonate and dried over anhydrous magnesium sulfate. After the solvent was distilled off under reduced pressure, the residue was subjected to column chromatography on silica gel (chloroform:methanol=19:1) to obtain 1.14 g of a yellow oil. The thus-obtained oil was dissolved in ammonia-containing methanol (3.6 ml), and Raney nickel (550 mg) was added to the solution. The mixture was shaken for 3 hours in a hydrogen atmosphere (3 kg/cm$^2$). The catalyst was removed by filtration through Celite, and the filtrate was concentrated under reduced pressure. The residue was subjected to column chromatography on Chromatolex NH silica (product of Fuji Silysia Co., Ltd.; chloroform:methanol:=20:1) to obtain 450 mg of the title compound.

mp: 42–45° C.; $^1$H-NMR (CDCl$_3$) δ: 2.80(2H,t,J=6.4 Hz), 3.02(2H,t,J=6.4 Hz), 6.96(2H,S), 8.01(1H,s). Mass (FAB (+)) m/e: 138 (MH)$^+$.

Preparation Example 26
2-(2-Methyl-5-nitro-1-imidazolyl)ethyl methanesulfonate:

Metronidazole (5.0 g, 29.2 mmol) was dissolved in pyridine (10 ml), and a pyridine solution (10 ml) of methanesulfonyl chloride (3.5 g, 30.7 mmol) was added dropwise to the solution. After the mixture was stirred at room temperature for 5 hours, the solvent was distilled off under reduced pressure, and the residue was washed with water-ethanol and dried to obtain 6.4 g of the title compound.

mp: 152–153° C.; $^1$H-NMR (DMSO-$d_6$) δ: 2.46(3H,s), 3.15(3H,s), 4.56(2H,t,J=4.9 Hz), 4.66(2H,t,J=4.9 Hz), 8.07 (1H,s). Mass (FAB(+)) m/e: 250 (MH)$^+$.

Preparation Example 27
(2-Methyl-5-nitro-1-imidazolyl)ethylazide:

The compound (1.99 g, 7.9 mmol) obtained in Preparation Example 26 was suspended in acetone (10 ml), and an aqueous solution (2 ml) of sodium azide (2.0 g, 31.5 mmol) and sodium iodide (110 mg, 0.7 mmol) were added to the suspension. The mixture was refluxed for 3 days. The solvent was distilled off under reduced pressure, and a 1N aqueous solution of sodium hydroxide was added to the residue. The mixture was extracted with ethyl acetate, and the extract was dried over anhydrous magnesium sulfate. The solvent was distilled off, and the residue was subjected to column chromatography on silica gel (chloroform:methanol:=20:1) to obtain 1.5 g of the title compound.

mp: 51.0–51.5° C.; $^1$H-NMR (DMSO-$d_6$) δ: 2.48(3H,s), 3.79(2H,t,J=5.8 Hz), 4.48(2H,t,J=5.8 Hz), 8.06(1H,s). Mass (FAB(+)) m/e: 197 (MH)$^+$.

Preparation Example 28
1-(2-Aminoethyl)-2-methyl-5-nitroimidazole:

The compound (1.5 g, 7.6 mmol) obtained in Preparation Example 27 was subjected to catalytic hydrogenation in accordance with the same process as in Preparation Example 11. The catalyst was removed by filtration through Celite, and the filtrate was subjected to column chromatography on silica gel (chloroform: methanol:=10:1) to obtain 450 mg of the title compound (frothy substance).

$^1$H-NMR (DMSO-$d_6$) δ: 2.47(3H,s), 2.88(2H,t,J=6.4 Hz), 3.34(2H,br.s), 4.27(2H,t,J=6.4 Hz), 8.02(1H,s). Mass (FAB (+)) m/e: 171 (MH)$^+$.

Preparation Example 29
2-(2-Aminoethylamino)-4-aminopyrimidine:

4-Benzoylamino-2-chloropyrimidine (2.34 g, 10.0 mmol) obtained in accordance with the process described in Japanese Patent Application Laid-Open No. 81375/1987 was stirred at 100° C. for 1 hour in ethylenediamine (12.1 g, 200.0 mmol). After completion of the reaction, ethylenediamine was distilled off under reduced pressure, and the residue was subjected to chromatography on CHP-20P gel (product of Mitsubishi Chemical Industries Ltd.; acetonitrile:water=10:90 to 15:85) to obtain 410 mg of the title compound.

$^1$H-NMR (DMSO-$d_6$) δ: 2.61(2H,t,J=6.2 Hz), 3.17(2H, dt,J=6.2,12.2 Hz), 2.0–3.6(2H,br.s), 5.66(1H,d,J=5.8 Hz), 6.23(3H,br.s), 7.65(1H,d,J=5.8 Hz). Mass (FAB(+)) m/e: 154 (MH)$^+$.

Preparation Example 30
N-{N-[(2S,3S)-3-trans-Carboxyoxirane-2-carbonyl]-L-phenylalanyl}-1,8-diaminooctane:

The title compound was synthesized in accordance with the process described in European Patent Publication No. 0655447A1.

mp: >210° C. (decomposed); $^1$H-NMR (DMSO-$d_6$) δ: 1.20–1.36(11H,m), 1.50–1.53(1H,m), 2.72(2H,t,J=7.3 Hz), 2.78(1H,dd,J=9.5,13.4 Hz), 2.89(1H,d,J=2.0 Hz), 2.92–2.96 (2H,m), 3.09–3.16(1H,m), 3.23(1H,d,J=1.7 Hz), 4.42(1H, dd,J=5.4,9.3 Hz), 7.16–7.27(5H,m), 7.92(1H,br.s). Mass (FAB(+)) m/e: 406 (MH)$^+$.

Example 1
N-{L-3-trans-[(4-Phenylpiperazin-1-yl)carbonyl]oxirane-2-carbonyl}-L-phenylalanine dimethylamide (Compound No. 1):

1-Hydroxybenzotriazole (149 mg, 1.1 mmol) and 1-ethyl-3-(3-dimethylaminopropyl)carbodiimide hydrochloride (230 mg, 1.2 mmol) were successively added to a solution (10 ml) with the compound obtained in Preparation Example 2 (306 mg, 1.0 mmol) and N-phenylpiperazine (162 mg, 1.0 mmol) dissolved in a mixed solvent of ethyl acetatetetrahydrofuran (1:1), and the mixture was stirred at room temperature for 3 hours. The reaction mixture was washed with water, diluted hydrochloric acid, a saturated aqueous solution of sodium hydrogencarbonate, water and saturated brine in that order, and dried over anhydrous magnesium sulfate. After the solvent was distilled off under reduced pressure, the resultant residue was subjected to chromatography on silica gel (ethyl acetate) to obtain 334 mg of the title compound.

mp: 72–74° C.; $^1$H-NMR (DMSO-$d_6$) δ: 2.80(3H,s), 2.83(1H,dd,J=8.6,13.7 Hz), 2.89(3H,s), 2.96(1H,dd,J=6.4, 13.4 Hz), 3.12(2H,t,J=5.0 Hz), 3.19(2H,t,J=4.9 Hz), 3.55–3.70(4H,m), 3.59(1H,d,J=1.9 Hz), 3.88(1H,d,J=2.0 Hz), 4.93–5.02(1H,m), 6.82(1H,t,J=7.2 Hz), 6.93–7.00(2H, m), 7.22–7.30(7H,m), 8.67(1H,d,J=8.3 Hz). Mass (FAB(+)) m/e: 451 (MH)$^+$.

Example 2

N-{L-3-trans-[2-(Benzenesulfonylamino)ethylcarbamoyl] oxirane-2-carbonyl}-L-phenylalanine dimethylamide (Compound No. 2):

Following a process similar to the process of Example 1, the title compound (1.1 g, foam) was obtained from the compound (1.1 g, 3.6 mmol) obtained in Preparation Example 2 and the compound (720 mg, 3.6 mmol) obtained in Preparation Example 11.

$^1$H-NMR (DMSO-$d_6$) δ: 2.75–2.85(3H,m), 2.78(3H,s), 2.88(3H,s), 2.94(1H,dd,J=6.1,13.4 Hz), 3.08–3.16(2H,m), 3.36(1H,d,J=1.7 Hz), 3.55(1H,d,J=1.7 Hz), 4.85–4.98(1H, m), 7.19–7.32(5H,m), 7.57–7.82(6H,m), 8.33(1H,t,J=5.6 Hz), 8.84(1H,d,J=8.3 Hz). Mass (FAB(+)) m/e: 489 (MH)$^+$.

Example 3

N-{L-3-trans-[2-(t-Butoxycarbonylaminomethyl) phenylcarbamoyl]oxirane-2-carbonyl}-L-phenylalanine dimethylamide (Compound No. 3):

Following a process similar to the process of Example 1, the title compound (780 mg, foam) was obtained from the compound (500 mg, 1.63 mmol) obtained in Preparation Example 2 and the compound (363 mg, 1.63 mmol) obtained in Preparation Example 7.

$^1$H-NMR (DMSO-$d_6$) δ: 1.38(9H,s), 2.78(3H,m), 2.83 (1H,dd,J=8.0,13.4 Hz), 2.87(3H,s), 2.96(1H,dd,J=6.1,13.2 Hz), 3.68(1H,d,J=1.0 Hz), 3.75(1H,d,J=1.7 Hz), 4.08(2H,d, J=5.9 Hz), 4.95(1H,dd,J=8.3,14.6 Hz), 7.12–7.43(10H,m), 8.99(1H,d,J=8.3 Hz), 9.94(1H,s). Mass (FAB(+)) m/e: 549 (M+K)$^+$.

Example 4

N-{L-3-trans-[2-(Aminomethyl)phenylcarbamoyl]oxirane-2-carbonyl}-L-phenylalanine dimethylamide hydrochloride (Compound No. 4):

The compound (200 mg, 0.39 mmol) obtained in Example 3 was suspended in chloroform (4 ml), and trifluoroacetic acid (2 ml) was added to the suspension under cooling with ice water to stir the mixture at room temperature for 40 minutes. A 4N hydrochloric acid/ethyl acetate solution (0.1 ml) was added to the reaction mixture under cooling with ice water, and the solvent was distilled off under reduced pressure. Chloroform and toluene were added to the residue, and the solvent was distilled off under reduced pressure to obtain the title compound (188 mg).

mp: 102–107° C.; $^1$H-NMR (DMSO-$d_6$) δ: 2.80(3H,s), 2.85(1H,dd,J=8.5,13.6 Hz), 2.89(3H,s), 2.98(1H,dd,J=6.4, 13.7 Hz), 3.76(1H,d,J=2.0 Hz), 3.78(2H,d,J=1.7 Hz), 4.00 (2H,br.d,J=5.6 Hz), 4.97(1H,dd,J=8.0,14.6 Hz), 7.23–7.51 (9H,m), 8.07(2H,br.s), 8.98(1H,d,J=8.0 Hz), 10.11(1H,s). Mass (FAB(+)) m/e: 411 (MH)$^+$.

Example 5

N-{L-3-trans-[3-(t-Butoxycarbonylaminomethyl) phenylcarbamoyl]oxirane-2-carbonyl}-L-phenylalanine dimethylamide (Compound No. 5):

Following a process similar to the process of Example 1, the title compound (740 mg, foam) was obtained from the compound (500 mg, 1.63 mmol) obtained in Preparation Example 2 and the compound (363 mg, 1.63 mmol) obtained in Preparation Example 8.

$^1$H-NMR (DMSO-$d_6$) δ: 1.40(9H,s), 2.79(3H,s), 2.83(1H, dd,J=8.3,13.4 Hz), 2.88(3H,s), 2.97(1H,dd,J=6.1,13.4 Hz), 3.67(1H,d,J=1.7 Hz), 3.70(1H,d,J=2.0 Hz), 4.09(2H,br.d,J= 6.3 Hz), 4.95(1H,dd,J=8.3,14.6 Hz), 6.97(1H,d,J=7.6 Hz), 7.21–7.50(9H,m), 8.99(1H,d,J=8.3 Hz), 10.43(1H,s). Mass (FAB(+)) m/e: 549 (M+K)$^+$.

Example 6

N-{L-3-trans-[3-(Aminomethyl)phenylcarbamoyl]oxirane-2-carbonyl}-L-phenylalanine dimethylamide hydrochloride (Compound No. 6):

Following a process similar to the process of Example 4, the title compound (195 mg) was obtained from the compound (200 mg, 0.39 mmol) obtained in Example 5.

mp: 107–112° C.; $^1$H-NMR (DMSO-$d_6$) δ: 2.79(3H,s), 2.84(1H,dd,J=8.6,13.4 Hz), 2.88(3H,s), 2.97(1H,dd,J=6.1, 13.4 Hz), 3.70(1H,d,J=1.7 Hz), 3.72(1H,d,J=1.7 Hz), 4.02 (2H,br.d,J=3.0 Hz), 4.95(1H,dd,J=8.3,14.6 Hz), 7.19–7.53 (8H,m), 7.79(1H,s), 8.15(2H,br.s), 8.99(1H,d,J=8.1 Hz), 10.55(1H,s). Mass (FAB(+)) m/e: 411 (MH)$^+$.

Example 7

N-{L-3-trans-[4-(t-Butoxycarbonylaminomethyl) phenylcarbamoyl]oxirane-2-carbonyl}-L-phenylalanine dimethylamide (Compound No. 7):

Following a process similar to the process of Example 1, the title compound (774 mg, foam) was obtained from the compound (500 mg, 1.63 mmol) obtained in Preparation Example 2 and the compound (363 mg, 1.63 mmol) obtained in Preparation Example 9.

$^1$H-NMR (DMSO-$d_6$) δ: 1.39(9H,s), 2.79(3H,s), 2.83(1H, dd,J=8.2,13.4 Hz), 2.88(3H,s), 2.96(1H,dd,J=6.1,13.4 Hz), 3.65(1H,d,J=1.7 Hz), 3.70(1H,d,J=1.7 Hz), 4.07(2H,d,J=6.1 Hz), 4.94(1H,dd,J=8.3,14.6 Hz), 7.13–7.36(7H,m), 7.53 (2H,d,J=8.3 Hz), 8.99(1H,d,J=8.0 Hz), 10.40(1H,s). Mass (FAB(+)) m/e: 549 (M+K)$^+$.

Example 8

N-{L-3-trans-[4-(Aminomethyl)phenylcarbamoyl]oxirane-2-carbonyl}-L-phenylalanine dimethylamide hydrochloride (Compound No. 8):

Following a process similar to the process of Example 4, the title compound (175 mg) was obtained from the compound (200 mg, 0.39 mmol) obtained in Example 7.

mp: 115–120° C.; $^1$H-NMR (DMSO-$d_6$) δ: 2.78(3H,s), 2.83(1H,dd,J=8.3,13.6 Hz), 2.88(3H,s), 2.97(1H,dd,J=6.1, 13.4 Hz), 3.68(1H,d,J=1.4 Hz), 3.72(1H,d,J=1.7 Hz), 3.99 (2H,br.s), 4.95(1H,dd,J=8.3,14.6 Hz), 7.23–7.32(5H,m), 7.41(2H,d,J=8.5 Hz), 7.65(2H,d,J=8.8 Hz), 8.15(2H,br.s), 8.98(1H,d,J=8.3 Hz), 10.55(1H,s). Mass (FAB(+)) m/e: 411 (MH)$^+$.

Example 9
N-[L-3-trans-(4-Benzylpiperazin-1-yl-carbonyl)oxirane-2-carbonyl]-L-phenylalanine dimethylamide (Compound No. 9):

Following a process similar to the process of Example 1, the title compound (155 mg, foam) was obtained from the compound (306 mg, 1.0 mmol) obtained in Preparation Example 2 and 1-benzylpiperazine (176 mg, 1.0 mmol).

$^1$H-NMR (DMSO-d$_6$) δ: 2.33(2H,t,J=4.9 Hz), 2.40(2H,t,J=4.9 Hz), 2.82(1H,dd,J=8.6,13.4 Hz), 2.87(3H,s), 2.89(3H,s), 2.94(1H,dd,J=6.3,13.4 Hz), 3.38–3.48(4H,m), 3.50(2H,s), 3.55(1H,d,J=1.9 Hz), 3.80(1H,d,J=2.0 Hz), 4.90–4.98 (1H,m), 7.13–7.35(10H,m), 8.13(1H,d,J=8.0 Hz). Mass (FAB(+)) m/e: 465 (MH)$^+$.

Example 10
N-{L-3-trans-[N-(2-t-Butoxycarbonylaminoethyl)-N-phenylcarbamoyl]oxirane-2-carbonyl}-L-phenylalanine dimethylamide (Compound No. 10):

Following a process similar to the process of Example 1, the title compound (206 mg, foam) was obtained from the compound (500 mg, 1.63 mmol) obtained in Preparation Example 2 and the compound (385 mg, 1.63 mmol) obtained in Preparation Example 10.

$^1$H-NMR (DMSO-d$_6$) δ: 1.32(9H,s), 2.76(1H,dd,J=7.8, 13.4 Hz), 2.80(3H,s), 2.81(3H,s), 2.89(1H,dd,J=6.1,13.4 Hz), 3.04(1H,d,J=1.7 Hz), 3.07(2H,br.d,J=6.1 Hz), 3.61(1H, d,J=1.7 Hz), 3.64–3.74(2H,m), 4.82(1H,dd,J=7.8,14.6 Hz), 6.94(1H,br.t,J=5.4 Hz), 7.10(2H,d,J=7.8 Hz), 7.17–7.46(8H, m), 8.68(1H,d,J=8.6 Hz). Mass (FAB(+)) m/e: 563 (M+K)$^+$.

Example 11
N-{L-3-trans-[N-(2-Aminoethyl)-N-phenylcarbamoyl]oxirane-2-carbonyl}-L-phenylalanine dimethylamide hydrochloride (Compound No. 11):

Following a process similar to the process of Example 4, the title compound (127 mg) was obtained from the compound (200 mg, 0.38 mmol) obtained in Example 10.

$^1$H-NMR (DMSO-d$_6$) δ: 2.76(1H,dd,J=8.0,13.4 Hz), 2.80 (3H,s), 2.81(3H,s), 2.86–2.94(2H,m),3.10(1H,d,J=2.0 Hz), 3.65(1H,d,J=1.7 Hz), 3.90(2H,br.t,J=5.6 Hz), 4.82(1H,dd,J=8.0,14.6 Hz), 7.08–7.49(10H,m), 7.82(2H,br.s), 8.61(1H,d, J=8.3 Hz). Mass (FAB(+)) m/e: 425 (MH)$^+$.

Example 12
N-{L-3-trans-[4-(t-Butoxycarbonylaminomethyl)phenylcarbamoyl]oxirane-2-carbonyl}-L-phenylalanine-2-phenylethylamide (Compound No. 12):

Following a process similar to the process of Example 1, the title compound (275 mg) was obtained from the compound (200 mg, 0.55 mmol) obtained in Preparation Example 6 and the compound (122 mg, 0.55 mmol) obtained in Preparation Example 9.

mp: 152.5–156° C.; $^1$H-NMR (DMSO-d$_6$) δ: 1.39(9H,s), 2.67(2H,t,J=7.1 Hz), 2.76(1H,dd,J=10.0,13.9 Hz), 2.94(1H, dd,J=4.9,13.9 Hz), 3.19–3.32(2H,m), 3.63(1H,d,J=1.7 Hz), 3.69(1H,d,J=1.7 Hz), 4.06(2H,d,J=5.8 Hz), 4.47–4.45(1H, m), 7.13–7.33(12H,m), 7.35(1H,t,J=7.0 Hz), 7.54(2H,d,J=8.6 Hz), 8.24(1H,d,J=5.6 Hz), 8.81(1H,d,J=8.5 Hz), 10.39 (1H,s). Mass (FAB(+)) m/e: 625 (M+K)$^+$.

Example 13
N-{L-3-trans-[4-(Aminomethyl)phenylcarbamoyl]oxirane-2-carbonyl}-L-phenylalanine-2-phenylethylamide hydrochloride (Compound No. 13):

Following a process similar to the process of Example 4, the title compound (69 mg) was obtained from the compound (130 mg, 0.23 mmol) obtained in Example 12.

mp: 152–154° C.; $^1$H-NMR (DMSO-d$_6$) δ: 2.68(2H,t,J=7.3 Hz), 2.77(1H,dd,J=10.0,13.7 Hz), 2.95(1H,dd,J=4.9, 13.7 Hz), 3.18–3.40(2H,m), 3.70(1H,s), 3.71(1H,s), 3.96 (2H,s), 4.48–4.57(1H,m), 7.15–7.33(10H,m), 7.45(2H,d,J=8.3 Hz), 7.66(2H,d,J=8.3 Hz), 8.23–8.37(4H,m), 8.84(1H, d,J=8.5 Hz), 10.67(1H,s). Mass (FAB(+)) m/e: 487 (MH)$^+$.

Example 14
N-[L-3-trans-(4-t-Butoxycarbonylpiperazin-1-yl-carbonyl)-oxirane-2-carbonyl]-L-phenylalanine dimethylamide (Compound No. 15):

Following a process similar to the process of Example 1, the title compound (240 mg) was obtained from the compound (306 mg, 1.0 mmol) obtained in Preparation Example 2 and 1-t-butoxycarbonylpiperazine (186 mg, 1.0 mmol).

mp: 159–160° C.; $^1$H-NMR (DMSO-d$_6$) δ: 1.41(9H,s), 2.79(3H,s), 2.82(1H,dd,J=4.9,13.4 Hz), 2.88(3H,s), 2.97 (1H,dd,J=7.0,13.2 Hz), 3.30–3.55(8H,m), 3.58(1H,d,J=1.9 Hz), 3.85(1H,d,J=1.6 Hz), 4.95(1H,ddd,J=6.4,8.4,8.5 Hz), 7.20–7.30(5H,m), 8.68(1H,d,J=8.3 Hz). Mass (FAB(+)) m/e: 513 (M+K)$^+$; (FAB(−)) m/e: 473 (M−H)$^−$.

Example 15
N-[L-3-trans-(Piperazin-1-yl-carbonyl)oxirane-2-carbonyl]-L-phenylalanine dimethylamide hydrochloride (Compound No. 16):

Following a process similar to the process of Example 4, the title compound (86 mg) was obtained from the compound (100 mg, 0.21 mmol) obtained in Example 14.

mp: 150–155° C.; $^1$H-NMR (DMSO-d$_6$) δ: 2.79(3H,s), 2.86(3H,s), 2.72–2.88(1H,m), 2.95(1H,dd,J=6.4,13.6 Hz), 3.02–3.50(4H,m), 3.63(1H,d,J=2.0 Hz), 3.65–3.85(4H,m), 3.91(1H,d,J=2.0 Hz), 4.88–5.00(1H,m), 7.21–7.31(5H,m), 8.04(1H,d,J=8.0 Hz). Mass (FAB(+)) m/e: 375 (MH)$^+$.

Example 16
N-{L-3-trans-[(1-Benzylpiperidin-4-yl)carbamoyl]oxirane-2-carbonyl}-L-phenylalanine dimethylamide hydrochloride (Compound No. 18):

Following a process similar to the process of Example 1, the title compound (244 mg) was obtained from the compound (306 mg, 1.0 mmol) obtained in Preparation Example 2 and 1-benzyl-4-aminopiperidine (190 mg, 1.0 mmol).

mp: 120–122° C.; $^1$H-NMR (DMSO-d$_6$) δ: 1.37–1.49(2H, m), 1.63–1.74(2H,m), 1.95–2.05(2H,m), 2.69–2.77(2H,m), 2.78(3H,s), 2.80(1H,dd,J=8.5,13.4 Hz), 2.87(3H,s), 2.93 (1H,dd,J=6.1,13.4 Hz), 3.41(1H,d,J=1.7 Hz), 3.47(2H,s), 3.50–3.62(1H,m), 3.57(1H,d,J=1.7 Hz), 4.85–4.95(1H,m), 7.22–7.33(10H,m), 8.33(1H,d,J=9.0 Hz), 8.92(1H,d,J=8.0 Hz). Mass (FAB(+)) m/e: 479 (MH)$^+$.

Example 17
N-{L-3-trans-[2-(Piperidin-1-yl)ethylcarbamoyl]oxirane-2-carbonyl}-L-phenylalanine dimethylamide hydrochloride (Compound No. 19):

Following a process similar to the process of Example 1, the title compound (270 mg) was obtained from the compound (306 mg, 1.0 mmol) obtained in Preparation Example 2 and 1-(2-aminoethyl)piperidine (128 mg, 1.0 mmol).

mp: 99–101° C.; $^1$H-NMR (DMSO-d$_6$) δ: 1.31–1.54(6H, m), 2.23–2.43(6H,m), 2.78(3H,s), 2.81(1H,dd,J=8.3,13.4 Hz), 2.87(3H,s), 2.94(1H,dd,J=6.2,13.4 Hz), 3.18(2H,dt,J=6.3,6.4 Hz), 3.43(1H,d,J=2.0 Hz), 3.55(1H,d,J=1.7 Hz), 4.91 (1H,ddd,J=6.1,6.3,8.3 Hz), 7.22–7.30(5H,m), 8.23(1H,t,J=5.5 Hz), 8.87(1H,d,J=8.1 Hz). Mass (FAB(+)) m/e: 417 (MH)$^+$.

Example 18
N-[L-3-trans-(4-Aminobenzylcarbamoyl)oxirane-2-carbonyl]-L-phenylalanine dimethylamide hydrochloride (Compound No. 20):

Following a process similar to the process of Example 1, the title compound (232 mg) was obtained from the compound (500 mg, 1.63 mmol) obtained in Preparation Example 2 and 4-aminobenzylamine (199 mg, 1.63 mmol).

mp: 118–123° C.; $^1$H-NMR (DMSO-d$_6$) δ: 2.79(3H,s), 2.81–2.84(1H,m), 2.88(3H,s), 2.95(1H,dd,J=6.1,13.4 Hz), 3.47(1H,d,J=2.0 Hz), 3.62(1H,d,J=2.0 Hz), 4.26(1H,dd,J=5.9,15.2 Hz), 4.32(1H,dd,J=6.6,15.0 Hz), 4.91(1H,dd,J=8.3, 14.4 Hz), 7.20–7.34(9H,m), 8.92–8.94(2H,m), 9.92 (2H.br.s). Mass (FAB(+)) m/e: 411 (MH)$^+$.

Example 19
N-{L-3-trans-[4-(Aminosulfonyl)phenylcarbamoyl] oxirane-2-carbonyl}-L-phenylalanine dimethylamide (Compound No. 21):

Following a process similar to the process of Example 1, the title compound (322 mg) was obtained from the compound (500 mg, 1.63 mmol) obtained in Preparation Example 2 and 4-aminobenzenesulforiamide (281 mg, 1.63 mmol).

mp: 163–175° C.; $^1$H-NMR (DMSO-d$_6$) δ: 1.89(3H,s), 2.72(1H,dd,J=8.6,13.7 Hz), 2.36(3H,s), 2.96(1H,dd,J=6.3, 13.4 Hz), 3.69(1H,d,J=1.7 Hz), 3.72(1H,d,J=1.7 Hz), 4.94 (H,dd,J=8.0,14.6 Hz), 7.17–7.31(9H,m), 9.00(1H,d,J=8.0 Hz), 10.73(1H,s). Mass (FAB(+)) m/e: 461 (MH)$^+$.

Example 20
N-{L-3-trans-[2-(Benzyloxycarbonylamino) ethylcarbamoyl]oxirane-2-carbonyl}-L-phenylalanine dimethylamide (Compound No. 22):

Following a process similar to the process of Example 1, the title compound (280 mg, foam) was obtained from the compound (306 mg, 1.0 mmol) obtained in Preparation Example 2 and N-benzyloxycarbonylethylenediamine hydrochloride (254 mg, 1.1 mmol) synthesized in accordance with the process described in Hoppe-Seyler's, Z. Physiol. Chem., 349, 251 (1968).

$^1$H-NMR (DMSO-d$_6$) δ: 2.78(3H,s), 2.82(1H,dd,J=8.8, 13.4 Hz), 2.88(3H,s), 2.94(1H,dd,J=6.1,13.4 Hz), 3.03–3.12 (2H,m), 3.12–3.11(2H,m), 3.39(1H,d,J=1.4 Hz), 3.58(1H,d, J=1.4 Hz), 4.80–4.95(4H,m), 5.01(2H,s), 7.23–7.60(11H, m), 8.37(1H,t,J=5.4 Hz), 8.84(1H,d,J=8.5 Hz). Mass (FAB (+)) m/e: 483 (MH)$^+$.

Example 21
N-{L-3-trans-[2-(t-Butoxycarbonylamino)ethylcarbamoyl] oxirane-2-carbonyl}-L-phenylalanine dime thylamide (Compound No. 23):

Following a process similar to the process of Example 1, the title compound (100 mg, foam) was obtained from the compound (306 mg, 1.0 mmol) obtained in Preparation Example 2 and N-t-butoxycarbonylethylenediamine (176 mg, 1.1 mmol).

$^1$H-NMR (DMSO-d$_6$) δ: 1.37(9H,s), 2.79(3H,s), 2.82(1H, dd,J=8.6,13.7 Hz), 2.88(3H,s), 2.93(1H,dd,J=6.1,13.7 Hz), 2.98(2H,dt,J=6.1,6.4 Hz), 3.11(dt,J=5.8,6.1 Hz), 3.39(1H,d, J=1.7 Hz), 3.58(1H,d,J=1.7 Hz), 4.91(1H,ddd,J=6.1,8.3,8.6 Hz), 6.86(1H,t,J=5.8 Hz), 7.20–7.40(5H,m), 8.32(1H,t,J= 6.4 Hz), 8.84(1H,d,J=8.3 Hz). Mass (FAB(+)) m/e: 487 (M+K)$^+$.

Example 22
N-{L-3-trans-[(2-Aminoethyl)carbamoyl]oxirane-2-carbonyl}-L-phenylalanine dimethylamide hydrochloride (Compound No. 24):

Following a process similar to the process of Example 4, the title compound (30 mg, foam) was obtained from the compound (100 mg, 0.22 mmol) obtained in Example 21.

$^1$H-NMR (DMSO-d$_6$): 2.75–2.93(3H,m), 2.79(3H,s), 2.88(3H,s), 2.95(1H,dd,J=6.1,13.4 Hz), 3.15–3.42(2H,m), 3.42(1H,d,J=1.3 Hz), 3.63(1H,d,J=1.3 Hz), 4.85–4.96(1H, m), 7.10–7.40(5H,m), 7.86(3H,br.s,), 8.50(1H,t,J=5.6 Hz), 8.82(1H,d,J=8.3 Hz). Mass (FAB(+)) m/e: 349 (MH)$^+$.

Example 23
N-[L-3-trans-(4-Piperonylpiperazin-1-yl-carbonyl)oxirane-2-carbonyl]-L-phenylalanine dimethylamide (Compound No. 25):

Following a process similar to the process of Example 1, the title compound (300 mg, foam) was obtained from the compound (306 mg, 1.0 mmol) obtained in Preparation Example 2 and 1-piperonylpiperazine (242 mg, 1.1 mmol).

$^1$H-NMR (DMSO-d$_6$) δ: 2.31(2H,dd,J=4.6,4.9 Hz), 2.38 (2H,dd,J=4.6,4.9 Hz), 2.79(3H,s), 2.82(1H,dt,J=8.6,13.4 Hz), 2.87(3H,s), 2.95(1H,dt,J=6.1,13.4 Hz), 3.34(2H,s), 3.32–3.59(4H,m), 3.56(1H,d,J=1.9 Hz), 3.80(1H,d,J=1.9 Hz), 4.95(1H,ddd,J=6.1,8.3,8.6 Hz), 5.99(2H,s), 6.72–6.78 (1H,m), 6.80–6.88(2H,m), 7.18–7.28(5H,m), 8.65(1H,d,J= 8.3 Hz). Mass (FAB(+)) m/e: 509 (MH)$^+$.

Example 24
N-{L-3-trans-[4-(t-Butoxycarbonylaminomethyl) phenylcarbamoyl]oxirane-2-carbonyl}-L-phenylalanine propylamide (Compound No. 26):

Following a process similar to the process of Example 1, the title compound (112 mg) was obtained from the compound (336 mg, 1.1 mmol) obtained in Preparation Example 4 and the compound (222 mg, 1.0 mmol) obtained in Preparation Example 9.

mp: 219–221° C.; $^1$H-NMR (DMSO-d$_6$) δ: 0.79(3H,t,J= 7.6 Hz), 1.28–1.44(2H,m), 1.39(9H,s), 2.81(1H,dd,J=9.5, 13.7 Hz), 2.90–3.09(3H,m), 3.63(1H,d,J=1.7 Hz), 3.69(1H, d,J=1.7 Hz), 4.07(2H,d,J=6.1 Hz), 4.47–4.57(1H,m), 7.12–7.32(7H,m), 7.35(1H,t,J=6.1 Hz), 7.53(2H,d,J=8.5 Hz), 8.11(1H,d,J=5.6 Hz), 8.21(1H,d,J=8.5 Hz), 10.39(1H, s). Mass (FAB(+)) m/e: 565 (M+K)$^+$.

Example 25
N-{L-3-trans-[(4-Aminomethyl)phenylcarbamoyl]oxirane-2-carbonyl}-L-phenylalanine propylamide hydrochloride (Compound No. 27):

Following a process similar to the process of Example 4, the title compound (47 mg) was obtained from the compound (100 mg, 0.19 mmol) obtained in Example 24.

mp: 149–152° C.; $^1$H-NMR (DMSO-d$_6$) δ: 0.79(3H,t,J= 7.3 Hz), 1.26–1.42(2H,m), 2.82(1H,dd,J=9.5,13.7 Hz), 2.90–3.05(3H,m), 3.67(1H,d,J=1.7 Hz), 3.72(1H,d,J=1.7 Hz), 3.97(2H,s), 4.45–4.59(1H,m), 7.16–7.34(5H,m), 7.43 (2H,d,J=8.6 Hz), 7.65(2H,d,J=8.6 Hz), 8.12(1H,t,J=5.6 Hz), 8.25(2H,br.s), 8.80(1H,d,J=8.6 Hz), 10.59(1H,s). Mass (FAB(+)) m/e: 425 (MH)$^+$.

Example 26
N-[L-3-trans-(4-Ethylphenylcarbamoyl)oxirane-2-carbonyl]-L- phenylalanine dimethylamide (Compound No. 29):

Following a process similar to the process of Example 1, the title compound (250 mg) was obtained from the compound (200 mg, 0.65 mmol) obtained in Preparation Example 2 and 4-ethylaniline (79 mg, 0.65 mmol).

mp: 89–94° C.; ¹H-NMR (DMSO-d₆) δ: 1.15(3H,t,J=7.6 Hz), 2.56(2H,dd,J=7.6,15.1 Hz), 2.79(3H,s), 2.88(3H,s), 2.83(1H,dd,J=8.3,13.7 Hz), 2.96(1H,dd,J=6.4,13.4 Hz), 3.64(1H,d,J=1.7 Hz), 3.70(1H,d,J=1.7 Hz), 4.94(1H,m), 7.16(2H,d,J=8.6 Hz), 7.21–7.32(5H,m), 7.51(2H,d,J=8.5 Hz), 8.99(1H,d,J=8.3 Hz), 10.34(1H,s). Mass (FAB(+)) m/e: 410 (MH)⁺.

Example 27

N-[L-3-trans-(Phenylcarbamoyl)oxirane-2-carbonyl]-L-phenylalanine dimethylamide (Compound No. 35):

Following a process similar to the process of Example 1, the title compound (392 mg) was obtained from the compound (306 mg, 1.0 mmol) obtained in Preparation Example 2 and aniline (93 mg, 1.0 mmol).

mp: 86–89° C.; ¹H-NMR (DMSO-d₆) δ: 2.79(3H,s), 2.83(1H,dd,J=8.3,13.3 Hz), 3.66(1H,d,J=1.7 Hz), 7.32(1H, d,J=1.7 Hz), 4.95(1H,m), 7.21–7.35(8H,m), 7.61(2H,d,J=7.6 Hz), 8.99(1H,d,J=8.3 Hz), 10.41(1H,s). Mass (FAB(+)) m/e: 382 (MH)⁺.

Example 28

N-[L-3-trans-(Pyridin-3-yl-carbamoyl)oxirane-2-carbonyl]-L-phenylalanine dimethylamide hydrochloride (Compound No. 36):

Following a process similar to the process of Example 1, the title compound (70 mg) was obtained from the compound (306 mg, 1.0 mmol) obtained in Preparation Example 2 and 3-aminopyridine (94 mg, 1.0 mmol).

mp: 140–147° C. (decomposed). ¹H-NMR (DMSO-d₆) δ: 2.78(3H,s), 2.83(1H,dd,J=5.8,11.2 Hz), 2.87(3H,s), 2.96 (1H,dd,J=6.4,13.7 Hz), 3.78(1H,d,J=1.9 Hz), 3.80(1H, J=1.7 Hz), 4.95(1H,m), 7.13–7.30(5H,m), 8.01(2H,d,J=7.1 Hz), 8.68(1H,d,J=7.1 Hz), 9.01(1H,d,J=7.8 Hz), 11.63(1H,s). Mass (FAB(+)) m/e: 383 (MH)⁺.

Example 29

N-[L-3-trans-(4-t-Butylphenylcarbamoyl)oxirane-2-carbonyl]-L-phenylalanine dimethylamide (Compound No. 37):

Following a process similar to the process of Example 1, the title compound (357 mg) was obtained from the compound (308 mg, 1.0 mmol) obtained in Preparation Example 2 and 4-t-butylaniline (179 mg, 1.2 mmol).

mp: 127.5–130° C.; ¹H-NMR (DMSO-d₆) δ: 1.26(9H,s), 2.79(3H,s), 2.83(1H,dd,J=8.4,13.2 Hz), 2.88(3H,s), 2.97 (1H,dd,J=6.4,13.2 Hz), 3.64(1H,d,J=2.0 Hz), 3.71(1H,d,J=2.0 Hz), 4.89–5.00(1H,m), 7.21–7.53(9H,m), 9.00(1H,d,J=8.1 Hz), 10.36(1H,s). Mass (FAB(+)) m/e: 438 (MH)⁺.

Example 30

N-{L-3-trans-[2-(2-t-Butoxycarbonylaminothiazol-4-yl) ethylcarbamoyl]oxirane-2-carbonyl}-L-phenylalanine dimethylamide (Compound No. 38):

Following a process similar to the process of Example 1, the title compound (1.29 g, foam) was obtained from the compound (806 mg, 2.63 mmol) obtained in Preparation Example 2 and the compound (640 mg, 2.63 mmol) obtained in Preparation Example 13.

¹H-NMR (DMSO-d₆) δ: 1.40(9H,s), 2.69(2H,dt,J=7.3, 14.6 Hz), 2.77(3H,s), 2.80(1H,dd,J=8.6,13.6 Hz), 2.86(3H, s), 2.93(1H,dd,J=6.1,13.4 Hz), 3.32–3.80(2H,m), 3.39(1H, d,J=1.4 Hz), 3.55(1H,d,J=1.5 Hz), 4.90(1H,m), 6.76(1H,s), 7.11–7.27(5H,m), 8.37(1H,t,J=5.8 Hz), 8.87(1H,d,J=8.3 Hz), 11.36(1H,br.s). Mass (FAB(+)) m/e: 532 (MH)⁺.

Example 31

N-{L-3-trans-[2-(2-Aminothiazol-4-yl)ethylcarbamoyl] oxirane-2-carbonyl}-L-phenylalanine dimethylamide hydrochloride (Compound No. 39):

Following a process similar to the process of Example 4, the title compound (783 mg) was obtained from the compound (1.28 g, 2.41 mmol) obtained in Example 30.

mp: 127.5–129° C.; ¹H-NMR (DMSO-d₆) δ: 2.63(2H,t, J=2.6 Hz), 2.77(3H,s), 2.81(1H,dd,J=8.3,12.9 Hz), 2.86(3H, s), 2.94(1H,dd,J=6.4,13.4 Hz), 3.30–3.37(2H,m), 3.38(1H, d,J=1.7 Hz), 3.54(1H,d,J=2.0 Hz), 4.88–4.93(1H,m), 6.50 (1H,s), 7.19–7.29(5H,m), 8.42(1H,t,J=5.8 Hz), 8.84(1H,d, J=8.3 Hz), 8.88(2H,br.s). Mass (FAB(+)) m/e: 432 (MH)⁺.

Example 32

N-[L-3-trans-(Quinolin-6-yl-carbamoyl)oxirane-2-carbonyl]-L-phenylalanine dimethylamide hydrochloride (Compound No. 40):

Following a process similar to the process of Example 1, the title compound (285 mg) was obtained from the compound (306 mg, 1.0 mmol) obtained in Preparation Example 2 and 6-aminoquinoline (114 mg, 1.0 mmol).

mp: 155° C. (decomposed).; ¹H-NMR (DMSO-d₆) δ: 2.73(3H,s), 2.80(3H,s), 2.85(1H,dd,J=8.6,14.0 Hz), 2.98 (1H,dd,J=6.4,13.4 Hz), 3.75(1H,s), 3.77(1H,s), 4.92–5.02 (1H,m), 7.28–7.34(5H,m), 7.50(1H,dd,J=4.2,4.2 Hz), 7.84 (1H,d,J=9.8 Hz), 7.95(1H,s), 7.99(1H,d,J=9.3 Hz), 8.32(1H, d,J=8.3 Hz), 8.39(1H,s), 8.81(1H,d,J=4.4 Hz), 9.03(1H,d,J=8.3 Hz), 10.8(1H,s). Mass (FAB(+)) m/e: 433 (MH)⁺.

Example 33

N-{L-3-trans-[(2-Methylisoxazol-4-yl)carbamoyl]oxirane-2-carbonyl}-L-phenylalanine dimethylamide (Compound No. 41):

Following a process similar to the process of Example 1, the title compound (320 mg) was obtained from the compound (2.0 g, 6.5 mmol) obtained in Preparation Example 2 and 2-methyl-4-aminoisoxazole (640 mg, 6.5 mmol).

mp: 80–82° C.; ¹H-NMR (DMSO-d₆) δ: 2.38(3H,s), 2.79(3H,s), 2.82(1H,dd,J=8.5,13.2 Hz), 2.87(3H,s), 2.96 (1H,dd,J=6.8,13.2 Hz), 3.70(2H,br.s), 4.89–4.98(1H,m), 6.61(1H,s), 7.19–7.34(5H,m), 8.95(1H,d,J=8.3 Hz), 11.53 (1H,s). Mass (FAB(+)) m/e: 387 (MH)⁺.

Example 34

N-{L-3-trans-[(4-Benzyloxycarbonylphenyl)carbamoyl] oxirane- 2-carbonyl}-L-phenylalanine dimethylamide (Compound No. 42):

Following a process similar to the process of Example 1, the title compound (606 mg, foam) was obtained from the compound (632 mg, 2.06 mmol) obtained in Preparation Example 2 and the compound (543 mg, 2.06 mmol) obtained in Preparation Example 14.

¹H-NMR (DMSO-d₆) δ: 2.79(3H,s), 2.83(1H,dd,J=8.3, 13.4 Hz), 2.88(3H,s), 2.97(1H,dd,J=6.6,13.4 Hz), 3.70(1H, d,J=1.7 Hz), 3.73(1H,d,J=1.7 Hz), 4.29–4.98(1H,m), 5.33 (2H,s), 7.21–7.47(10H,m), 7.77(2H,d,J=8.8 Hz), 7.98(2H,d, J=8.8 Hz), 8.99(1H,d,J=8.3 Hz), 10.75(1H,s). Mass (FAB (+)) m/e: 516 (MH)⁺.

Example 35

N-[L-3-trans-(4-Carboxyphenylcarbamoyl)oxirane-2-carbonyl]-L-phenylalanine dimethylamide (Compound No. 43):

10% Palladium on carbon (200 mg) was added to a methanol solution (50 ml) of the compound (606 mg, 1.18 mmol) obtained in Example 34, and the mixture was stirred at room temperature for 1.5 hours in a hydrogen atmosphere.

After completion of the reaction, the catalyst was separated by filtration, and the filtrate was concentrated under reduced pressure to obtain 474 mg of the title compound.

mp: 105–107° C.; $^1$H-NMR (DMSO-d$_6$) δ: 2.79(3H,s), 2.83(1H,dd,J=10.0,15.1 Hz), 2.88(3H,s), 2.97(1H,dd,J=6.3, 13.6 Hz), 3.70(1H,d,J=1.7 Hz), 3.73(1H,d,J=1.7 Hz), 4.29–4.98(1H,m), 7.23–7.32(5H,m), 7.73(2H,d,J=8.8 Hz), 7.91(2H,d,J=8.8 Hz), 9.01(1H,d,J=8.3 Hz), 10.71(1H,s). Mass (FAB(−)) m/e: 424 (M−H)$^−$.

Example 36

N-{L-3-trans-[4-(Benzoylaminomethyl)phenylcarbamoyl]oxirane-2-carbonyl}-L-phenylalanine dimethylamide (Compound No. 44):

The compound (200 mg, 0.45 mmol) obtained in Example 8 and triethylamine (91 mg, 0.89 mmol) were dissolved in dichloromethane (10 ml), and benzoyl chloride (69 mg, 0.49 mmol) was added to the solution under cooling with ice water. The mixture was stirred for 2.5 hours as it was. After the reaction mixture was diluted with chloroform, it was washed with water, diluted hydrochloric acid, a saturated aqueous solution of sodium hydrogencarbonate and saturated brine and dried over anhydrous magnesium sulfate. The solvent was distilled off under reduced pressure, and the resultant residue was subjected to column chromatography on silica gel (chloroform:methanol=20:1) to obtain 146 mg of the title compound.

mp: 104–107° C.; $^1$H-NMR (DMSO-d$_6$) δ: 2.79(3H,s), 2.82(1H,dd,J=8.5,13.6 Hz), 2.88(3H,s), 2.96(1H,dd,J=6.3, 13.4 Hz), 3.65(1H,d,J=1.4 Hz), 3.71(1H,d,J=1.7 Hz), 4.44 (2H,d,J=5.9 Hz), 4.91–4.97(1H,m), 7.21–7.31(7H,m), 7.45–7.54(5H,m), 7.89(2H,d,J=7.1 Hz), 8.97–9.02(2H,m), 10.41(1H,s). Mass (FAB(+)) m/e: 515 (MH)$^+$.

Example 37

N-{L-3-trans-[2-(5-Nitropyridin-2-yl)aminoethylcarbamoyl]oxirane-2-carbonyl}-L-phenylalanine dimethylamide (Compound No. 46):

Following a process similar to the process of Example 1, the title compound (1.55 g) was obtained from the compound (1.22 g, 4.0 mmol) obtained in Preparation Example 2 and 2-(2-aminoethylamino)-5-nitropyridine (729 mg, 4.0 mmol).

mp: 77–79° C.; $^1$H-NMR (DMSO-d$_6$) δ: 2.79(3H,s), 2.81(1H,dd,J=8.4,13.4 Hz), 2.88(3H,s), 2.94(1H,dd,J=6.3, 13.6 Hz), 3.25–3.35(2H,m), 3.41(1H,d,J=1.7 Hz), 3.47(2H,br.m), 3.59(1H,d,J=1.7 Hz), 4.91(1H,dt,J=6.4,8.2 Hz), 6.56 (1H,d,J=9.5 Hz), 7.18–7.32(5H,m), 8.05–8.15(1H,m), 8.15–8.25(1H,m), 8.47(1H,t,J=5.6 Hz), 8.83(1H,d,J=8.0 Hz), 8.92(1H,d,J=2.7 Hz). Mass (FAB(+)) m/e: 471 (MH)$^+$.

Example 38

N-{L-3-trans-[(4-Ethenylphenyl)carbamoyl]oxirane-2-carbonyl}-L-phenylalanine dimethylamide (Compound No. 47):

Following a process similar to the process of Example 1, the title compound (397 mg) was obtained from the compound (306 mg, 1.0 mmol) obtained in Preparation Example 2 and 4-aminostyrene (119 mg, 1.0 mmol).

mp: 78–80° C.; $^1$H-NMR (DMSO-d$_6$) δ: 2.79(3H,s), 2.83(1H,dd,J=8.6,13.7 Hz), 2.88(1H,s), 2.97(1H,dd,J=6.4, 13.4 Hz), 3.66(1H,d,J=1.7 Hz), 3.71(1H,d,J=2.0 Hz), 4.95 (1H,dd,J=8.3,14.6 Hz), 5.20(1H,d,J=11.7 Hz), 5.76(1H,d,J= 17.8 Hz), 6.68(1H,dd,J=11.0,17.8 Hz), 7.14–7.32(5H,m), 7.44(2H,d,J=8.5 Hz), 7.60(2H,d,J=8.6 Hz), 8.99(1H,d,J=8.3 Hz), 10.47(1H,s). Mass (FAB(+)) m/e: 408 (MH)$^+$.

Example 39

N-[L-3-trans-(4-Phenoxyphenylcarbamoyl)oxirane-2-carbonyl]-L-phenylalanine dimethylamide (Compound No. 48):

Following a process similar to the process of Example 1, the title compound (295 mg) was obtained from the compound (200 mg, 0.65 mmol) obtained in Preparation Example 2 and 4-phenoxyaniline (121 mg, 0.65 mmol).

mp: 107–109° C.; $^1$H-NMR (DMSO-d$_6$) δ: 2.79(3H,s), 2.83(1H,dd,J=5.1,13.6 Hz), 2.88(3H,s), 2.97(1H,dd,J=6.1, 13.4 Hz), 3.65(1H,d,J=1.7 Hz), 3.72(1H,d,J=1.7 Hz), 4.92–4.98(1H,m), 6.96–4.40(12H,m), 7.62(2H,d,J=9.0 Hz), 8.99(2H,d,J=8.3 Hz), 10.44(1H,s). Mass (FAB(+)) m/e: 474 (MH)$^+$.

Example 40

N-{L-3-trans-[N-(4-Ethylphenyl)-N-methylcarbamoyl]oxirane-2-carbonyl}-L-phenylalanine dimethylamide (Compound No. 31):

Following a process similar to the process of Example 1, the title compound (420 mg, foam) was obtained from the compound (306 mg, 1.0 mmol) obtained in Preparation Example 2 and the compound (142 mg, 1.05 mmol) obtained in Preparation Example 15.

$^1$H-NMR (DMSO-d$_6$) δ: 1.17(3H,t,J=7.6 Hz), 2.61(2H,q, J=7.6 Hz), 2.77(1H,dd,J=8.1,13.4 Hz), 2.81(6H,s), 2.90(1H, dd,J=6.4,13.4 Hz), 3.20(3H,s), 3.32(2H,br.s), 4.79–4.89(1H, m), 7.09–7.31(9H,m), 8.74(1H,d,J=8.3 Hz). Mass (FAB(+)) m/e: 424 (MH)$^+$.

Example 41

N-[L-3-trans-(4-Ethylphenylcarbamoyl)oxirane-2-carbonyl]-L-phenylalanine propylamide (Compound No. 32):

Following a process similar to the process of Example 1, the title compound (588 mg) was obtained from the compound (500 mg, 1.56 mmol) obtained in Preparation Example 4 and 4-ethylaniline (189 mg, 1.56 mmol).

mp: 224–226° C.; $^1$H-NMR (DMSO-d$_6$) δ: 0.79(3H,t,J= 7.3 Hz), 1.15(3H,t,J=7.6 Hz), 1.31–1.39(2H,m), 2.56(1H, dd,J=7.3,14.9 Hz), 2.81(1H,dd,J=9.5,13.4 Hz), 3.62(1H,d, J=1.7 Hz), 3.69(1H,d,J=1.4 Hz), 4.50–4.55(1H,m), 7.16(2H, d,J=8.3 Hz), 7.20–7.31(5H,m), 7.51(2H,d,J=8.3 Hz), 8.1 (1H,t,J=5.6 Hz), 8.81(2H,d,J=8.3 Hz), 10.34(1H,s). Mass (FAB(+)) m/e: 424 (MH)$^+$.

Example 42

N-[D-3-trans-(4-Ethylphenylcarbamoyl)oxirane-2-carbonyl]-L-phenylalanine dimethylamide (Compound No. 49):

Following a process similar to the process of Example 1, the title compound (2.5 g) was obtained from the compound (2.4 g, 7.9 mmol) obtained in Preparation Example 16 and 4-ethylaniline (1.06 g, 8.7 mmol).

mp: 143–145° C.; $^1$H-NMR (DMSO-d$_6$) δ: 1.16(3H,t,J= 7.8 Hz), 2.56(1H,q,J=7.8 Hz), 2.80(3H,s), 2.82(1H,dd,J= 8.3,13.7 Hz), 2.87(3H,s), 2.97(1H,dd,J=6.8,13.7 Hz), 3.63 (1H,s), 3.71(1H,s), 4.88–4.98(1H,m), 7.14–7.31(7H,m), 7.51(2H,d,J=8.0 Hz), 8.91(1H,d,J=8.3 Hz), 10.35(1H,s). Mass (FAB(+)) m/e: 410 (MH)$^+$.

Example 43

N-[L-3-trans-(Benzylcarbamoyl)oxirane-2-carbonyl]-L-phenylalanine dimethylamide (Compound No. 50):

Following a process similar to the process of Example 1, the title compound (220 mg, amorphous substance) was obtained from the compound (200 mg, 0.65 mmol) obtained in Preparation Example 2 and benzylamine (70 mg, 0.65 mmol).

¹H-NMR (DMSO-d₆) δ: 2.78(3H,s), 2.81(1H,dd,J=8.6, 13.4 Hz), 2.88(3H,s), 2.95(1H,dd,J=6.1,13.4 Hz), 3.47(1H, d,J=1.7 Hz), 3.62(1H,d,J=2.0 Hz), 4.27(1H,dd,J=5.8,14.9 Hz), 4.32(1H,dd,J=6.6,15.4 Hz), 4.89–4.95(1H,m), 7.20–7.35(10H,m), 8.86(1H,t,J=6.4 Hz), 8.92(1H,d,J=8.3 Hz). Mass (FAB(+)) m/e: 396 (MH)⁺.

Example 44

N-[L-3-trans-(2-Phenylethylcarbamoyl)oxirane-2-carbonyl]-L-phenylalanine dimethylamide (Compound No. 53):

Following a process similar to the process of Example 1, the title compound (272 mg, amorphous substance) was obtained from the compound (612 mg, 2.0 mmol) obtained in Preparation Example 2 and 2-phenylethylamine (254 mg, 2.0 mmol).

¹H-NMR (DMSO-d₆) δ: 2.73(2H,t,J=7.4 Hz), 2.79(3H,s), 2.81(1H,dd,J=8.6,13.4 Hz), 2.87(3H,s), 2.95(1H,dd,J=6.2, 13.5 Hz), 3.28–3.35(2H,m), 3.39(1H,d,J=2.0 Hz), 3.55(1H, d,J=1.7 Hz), 4.88–4.95(1H,m), 7.16–7.35(10H,m), 8.41(1H, t,J=5.4 Hz), 8.86(1H,d,J=8.3 Hz). Mass (FAB(+)) m/e: 410 (MH)⁺.

Example 45

N-{L-3-trans-[2-(Pyridin-2-yl)ethylcarbamoyl]oxirane-2-carbonyl}-L-phenylalanine dimethylamide (Compound No. 56):

Following a process similar to the process of Example 1, the title compound (650 mg) was obtained from the compound (1.22 g, 4.0 mmol) obtained in Preparation Example 2 and 2-(2-aminoethyl)pyridine (538 mg, 4.0 mmol).

mp: 123–124° C.; ¹H-NMR (DMSO-d₆) δ: 2.79(3H,s), 2.81(1H,dd,J=8.3,13.4 Hz), 2.87(3H,s), 2.88(2H,t,J=7.6 Hz), 2.94(1H,dd,J=6.1,13.4 Hz), 3.39(1H,d,J=0.8 Hz), 3.45 (2H,dt,J=6.6,6.9 Hz), 3.55(1H,d,J=1.2 Hz), 4.87–4.95(1H, m), 7.08–7.33(7H,m), 7.71(1H,dd,J=7.6,7.8 Hz), 8.42(1H,t, J=5.8 Hz), 8.50(1H,d,J=4.6 Hz), 8.86(1H,d,J=8.3 Hz). Mass (FAB(+)) m/e: 411 (MH)⁺.

Example 46

N-{D-3-trans-[(2-Phenylethyl)carbamoyl]oxirane-2-carbonyl}-L-phenylalanine dimethylamide (Compound No. 60):

Following a process similar to the process of Example 1, the title compound (1.04 g) was obtained from the compound (1.02 g, 3.3 mmol) obtained in Preparation Example 16 and 2-phenylethylamine (427 mg, 3.3 mmol).

mp: 140–147° C. (decomposed).; ¹H-NMR (DMSO-d₆) δ: 2.73(2H,t,J=7.3 Hz), 2.78(3H,s), 2.80(1H,dd,J=5.1,13.7 Hz), 2.85(3H,s), 2.95(1H,dd,J=6.5,13.7 Hz), 3.29–3.35(2H, m), 3.38(1H,d,J=1.7 Hz), 3.55(1H,d,J=1.7 Hz), 4.86–4.92 (1H,m), 7.15–7.34(10H,m), 8.41(2H,t,J=5.6 Hz), 8.85(1H, d,J=8.0 Hz). Mass (FAB(+)) m/e: 410 (MH)⁺.

Example 47

N-{D-3-trans-[2-(Pyridin-2-yl)ethylcarbamoyl]oxirane-2-carbonyl}-L-phenylalanine dimethylamide (Compound No. 61):

Following a process similar to the process of Example 1, the title compound (630 mg) was obtained from the compound (1.02 g, 3.3 mmol) obtained in Preparation Example 16 and 2-(2-aminoethyl)pyridine (428 mg, 3.3 mmol).

mp: 143–144° C.; ¹H-NMR (DMSO-d₆) δ: 2.78(3H,s), 2.81(1H,dd,J=5.4,13.7 Hz), 2.85(3H,s), 2.88(2H,t,J=7.2 Hz), 2.94(1H,dd,J=6.6,13.7 Hz), 3.37(1H,s), 3.43–3.48(2H, m), 3.55(1H,s), 4.87–4.92(1H,m), 7.18–7.30(7H,m), 7.71 (1H,dd,J=7.3,8.0 Hz), 8.42(1H,t,J=5.6 Hz), 8.50(1H,d,J=4.6 Hz), 8.85(1H,d,J=8.1 Hz). Mass (FAB(+)) m/e: 411 (MH)⁺.

Example 48

N-{L-3-trans-[2-(Pyridin-2-yl)ethylcarbamoyl]oxirane-2-carbonyl}-L-phenylalanine methylamide (Compound No. 62):

The compound (500 mg, 1.71 mmol) obtained in Preparation Example 20 and 2-(2-aminoethyl)pyridine (209 mg, 1.17 mmol) were dissolved in N,N-dimethylformamide (10 ml), and 1-hydroxybenzotriazole (254 mg, 1.88 mmol) and 1-ethyl-3-(3-dimethylaminopropyl)carbodiimide hydrochloride (3.96 mg, 2.05 mmol) were added to the solution under cooling with ice water. The mixture was stirred at room temperature for 2 hours. The reaction mixture was diluted with ethyl acetate and washed with water and a saturated aqueous solution of sodium hydrogencarbonate. The washings were collected, saturated with sodium chloride and then extracted twice with ethyl acetate. Organic phases were collected and dried over anhydrous magnesium sulfate. After the desiccant was separated by filtration, the filtrate was concentrated under reduced pressure, and the resultant solids were washed with diisopropyl ether to obtain 217 mg of the title compound.

mp: 204–208° C.; ¹H-NMR (DMSO-d₆) δ: 2.58(3H,d,J= 4.3 Hz), 2.78(1H,dd,J=9.8,13.4 Hz), 2.86–2.90(2H,m), 3.00 (1H,dd,J=4.6,13.6 Hz), 3.45(2H,dd,J=7.3,13.7 Hz), 3.53 (1H,d,J=1.9 Hz), 4.46(1H,ddd,J=4.9,9.3,9.3 Hz), 7.18–7.30 (9H,m), 7.71(1H,ddd,J=1.9,7.8,7.8 Hz), 8.06(1H,d,J=4.9 Hz), 8.42(1H,dd,J=8.4,8.4 Hz), 8.50(1H,dd,J=0.8,4.9 Hz), 8.71(1H,d,J=8.6 Hz). Mass (FAB(+)) m/e: 397 (MH)⁺.

Example 49

N-{L-3-trans-[2-(1H-Imidazol-4-yl)ethylcarbamoyl]oxirane-2-carbonyl}-L-phenylalanine dimethylamide (Compound No. 63):

The compound (1.5 g, 4.9 mmol) obtained in Preparation Example 2 was dissolved in acetonitrile (10 ml), and triethylamine (0.55 g, 5.4 mmol) was added to the solution. Phosphorus oxychloride (0.83 g, 5.4 mmol) was added dropwise to the mixture under cooling with ice water and stirred for 15 minutes. Histamine dihydrochloride (850 mg, 4.7 mmol) was then added little by little to stir the resultant mixture at room temperature for 4 hours. The reaction mixture was concentrated under reduced pressure. After a 1N aqueous solution of sodium hydroxide was added to the resultant residue to alkalify it to pH 9, the residue was extracted with ethyl acetate. After the solvent was distilled off, the resultant residue was subjected to column chromatography on silica gel (chloroform:methanol=3:1 to 1:1) to obtain 150 mg of the title compound.

mp: 170° C. (decomposed).; ¹H-NMR (DMSO-d₆) δ: 2.51–2.55(2H,m), 2.79(3H,s), 2.81(1H,dd,J=8.1,13.4 Hz), 2.88(3H,s), 2.95(1H,dd,J=6.1,13.4 Hz), 3.20–3.45(2H,m), 3.40(1H,d,J=1.2 Hz), 3.57(1H,d,J=1.2 Hz), 4.91(1H,ddd,J= 6.1,8.1,8.3 Hz), 6.81(1H,s), 7.17–7.31(5H,m), 7.54(1H,s), 8.40(1H,t,J=5.8 Hz), 8.87(1H,d,J=8.3 Hz), 11.85(1H,brs). Mass (FAB(+)) m/e: 400 (MH)⁺.

Example 50

N-{L-3-trans-{N-[2-(Pyridin-2-yl)ethyl]-N-methylcarbamoyl}oxirane-2-carbonyl}-L-phenylalanine dimethylamide (Compound No. 64):

Following a process similar to the process of Example 49, the title compound (450 mg, foam) was obtained from the compound (1.0 g, 3.26 mmol) obtained in Preparation Example 2 and betahistine dimethanesulfonate (1.0 g, 3.10 mmol).

¹H-NMR (DMSO-d₆) δ: 2.77–3.10(13H,m), 3.33(0.5H,d, J=1.7 Hz), 3.46(0.5H,d,J=1.7 Hz), 2.60–3.90(2H,m), 3.73 (0.5H,d,J=1.7 Hz), 3.75(0.5H,d,J=1.7 Hz), 4.90–5.05(1H, m), 7.18–7.34(7H,m), 7.65–7.74(1H,m), 8.46(0.5H,d,J=4.6 Hz), 8.49(0.5H,d,J=4.6 Hz), 8.66(0.5H,d,J=8.3 Hz), 8.73 (0.5H,d,J=8.3 Hz). Mass (FAB(+)) m/e: 425 (MH)$^+$.

Example 51
N-{L-3-trans-[3-(Imidazol-1-yl)propylcarbamoyl]oxirane-2-carbonyl}-L-phenylalanine dimethylamide (Compound No. 65):

Following a process similar to the process of Example 49, the title compound (644 mg, foam) was obtained from the compound (766 mg, 2.5 mol) obtained in Preparation Example 2 and 1-(3-aminopropyl)imidazole.

$^1$H-NMR (DMSO-d$_6$) δ: 1.82–1.85(2H,m), 2.78(3H,s), 2.80(1H,dd,J=8.1,13.1 Hz), 2.87(1H,s), 2.94(1H,dd,J=6.1, 13.1 Hz), 3.00–3.10(2H,m), 3.97(2H,t,J=7.2 Hz), 3.40(1H, d,J=2.0 Hz), 3.58(1H,d,J=2.0 Hz), 4.92(1H,ddd,J=6.1,8.1, 8.2 Hz), 6.88(1H,d,J=1.0 Hz), 7.17(1H,d,J=1.0 Hz), 7.20–7.30(5H,m), 7.61(1H,s), 8.38(1H,t,J=5.6 Hz), 8.89 (1H,d,J=8.3 Hz). Mass (FAB(+)) m/e: 414 (MH)$^+$.

Example 52
N-{L-3-trans-[2-(6-Aminopyridin-2-yl)ethylcarbamoyl]oxirane-2-carbonyl}-L-phenylalanine dimethylamide (Compound No. 69):

Following a process similar to the process of Example 49, the title compound (680 mg, foam) was obtained from the compound (1.19 g, 3.89 mmol) obtained in Preparation Example 2 and 6-amino-2-(2-aminoethyl)pyridine (535 mg, 3.89 mmol) obtained in accordance with the process described in International Publication No. WO97-09982.

$^1$H-NMR (CDCl$_3$) δ: 2.69(3H,s), 2.72–2.78(2H,m), 2.88 (3H,s), 2.98(1H,m), 3.36(1H,d,J=2.0 Hz), 3.43(1H,d,J=2.0 Hz), 3.45–3.55(1H,m), 3.56–3.66(1H,m), 4.54(2H,s), 5.12 (1H,ddd,J=6.2,8.4,8.6 Hz), 6.35(1H,d,J=8.4 Hz), 6.47(1H, d,J=8.4 Hz), 7.15(1H,br.s), 7.25–7.35(5H,m), 7.49(1H,br.s). Mass (FAB(+)) m/e: 426 (MH)$^+$.

Example 53
N-{L-3-trans-[2-(4-Aminophenyl)ethylcarbamoyl]oxirane-2-carbonyl}-L-phenylalanine dimethylamide (Compound No. 73):

2-(4-Aminophenyl)ethylamine (454 mg, 3.3 mmol) was dissolved in ethyl acetate (20 ml), and a solution with the compound (1.37 g, 3.3 mmol) obtained in Preparation Example 21 dissolved in ethyl acetate (5 ml) was added dropwise under cooling with ice water. After completion of the addition, the solvent was distilled off, and the residue was subjected to column chromatography on silica gel (chloroform:methanol=30:1) to obtain 650 mg of the title compound (foam).

$^1$H-NMR (DMSO-d$_6$) δ: 2.45–2.55(2H,m), 2.79(3H,s), 2.81(1H,dd,J=8.5,13.4 Hz), 2.87(3H,s), 2.94(1H,dd,J=6.1, 13.4 Hz), 3.05–3.25(2H,m), 3.39(1H,d,J=1.7 Hz), 3.55(1H, d,J=1.7 Hz), 4.86(2H,brs), 4.89(1H,ddd,J=6.1,8.1,8.5 Hz), 6.49(2H,d,J=8.3 Hz), 6.84(2H,d,J=8.3 Hz), 7.20–7.30(5H, m), 8.35(1H,d,J=5.6 Hz), 8.86(1H,d,J=8.1 Hz). Mass (FAB (+)) m/e: 425 (MH)$^+$.

Example 54
N-{L-3-trans-[2-(Imidazol-1-yl)ethylcarbamoyl]oxirane-2-carbonyl}-L-phenylalanine dimethylamide (Compound No. 75):

Following a process similar to the process of Example 53, the title compound (1.02 g, foam) was obtained from the compound (1.39 g, 3.23 mmol) obtained in Preparation Example 21 and 1-(2-aminoethyl)-imidazole (300 mg, 2.69 mmol) obtained in accordance with the process described in J. Heterocyclic Chem., 14, 1279 (1977).

$^1$H-NMR (DMSO-d$_6$) δ: 2.79(3H,s), 2.82(1H,dd,J=8.8, 13.4 Hz), 2.87(3H,s), 2.95(1H,dd,J=6.1,13.4 Hz), 3.26–3.41 (2H,br.s), 3.40(1H,s), 3.54(1H,s), 4.04(2H,t,J=6.1 Hz), 4.92 (1H,ddd,J=6.1,8.3,8.8 Hz), 6.88(1H,s), 7.14(1H,s), 7.17–7.33(5H,m), 7.57(1H,s), 8.44(1H,t,J=6.4 Hz), 8.88 (1H,d,J=8.3 Hz). Mass (FAB(+)) m/e: 400 (MH)$^+$.

Example 55
N-{L-3-trans-[3-(4-Aminoimidazol-1-yl)propylcarbamoyl]oxirane-2-carbonyl}-L-phenylalanine dimethylamide (Compound No. 76):

Following a process similar to the process of Example 49, the title compound (180 mg, foam) was obtained from the compound (1.0 g, 3.28 mmol) obtained in Preparation Example 2 and the compound (460 mg, 3.28 mmol) obtained in Preparation Example 24.

$^1$H-NMR (DMSO-d$_6$) δ: 1.85–2.0(2H,m), 2.79(3H,s), 2.83(1H,dd,J=8.1,13.1 Hz), 2.88(3H,s), 2.96(1H,dd,J=6.2, 13.4 Hz), 3.02–3.09(2H,m), 3.91–3.99(2H,m), 3.43(1H,d,J= 2.0 Hz), 3.58(1H,d,J=2.0 Hz), 4.95(1H,ddd,J=6.2,8.1,8.3 Hz), 5.60(2H,s), 6.99(1H,s), 7.21–7.31(5H,m), 7.82(1H,s), 8.90(1H,d,J=8.2 Hz). Mass (FAB(+)) m/e: 429 (MH)$^+$.

Example 56
N-{L-3-trans-[2-(5-Aminopyridin-2-yl)ethylcarbamoyl]oxirane-2-carbonyl}-L-phenylalanine dimethylamide (Compound No. 77):

The compound (446 mg, 1.45 mmol) obtained in Preparation Example 2 was dissolved in acetonitrile (50 ml), and 4-nitrophenol (202 mg, 1.45 mmol) and 1-ethyl-3-(dimethylaminopropyl)carbodiimide hydrochloride (307 mg, 1.60 mmol) were added to the solution. The compound (200 mg, 1.45 mmol) obtained in Preparation Example 25 was then added, and the resultant mixture was stirred at room temperature for 4 hours. The reaction mixture was diluted with ethyl acetate, washed with a saturated aqueous solution of sodium hydrogencarbonate and saturated brine in that order, and then dried over anhydrous magnesium sulfate. After the solvent was distilled off, the resultant residue was subjected to column chromatography on silica gel (chloroform:methanol=10:1) to obtain 480 mg of the title compound (foam).

$^1$H-NMR (DMSO-d,) δ: 2.67(2H,t,J=7.9 Hz), 2.79(3H,s), 2.85(1H,dd,J=8.4,13.3 Hz), 2.87(3H,s), 2.95(1H,dd,J=6.2, 13.3 Hz), 3.39(1H,d,J=1.9 Hz), 3.55(1H,d,J=1.9 Hz), 4.91 (1H,ddd,J=6.2,8.4,8.6 Hz), 5.20(2H,s), 6.83–6.89(2H,m), 7.20–7.30(5H,m), 7.80(1H,s), 8.34(1H,br.s), 8.85(1H,d,J= 8.1 Hz). Mass (FAB(+)) m/e: 426 (MH)$^+$.

Example 57
N-{L-3-trans-[(1H-Benzimidazol-2-yl)methylcarbamoyl]oxirane-2-carbonyl}-L-phenylalanine dimethylamide (Compound No. 78):

Following a process similar to the process of Example 1, the title compound (1.2 g, foam) was obtained from the compound (1.0 g, 3.3 mmol) obtained in Preparation Example 2 and 2-aminomethylbenzimidazole dihydrochloride (720 mg, 3.3 mmol).

$^1$H-NMR (DMSO-d$_6$) δ: 2.79(3H,s), 2.83(1H,dd,J=8.6, 13.3 Hz), 2.89(3H,s), 2.95(1H,dd,J=6.4,13.3 Hz), 3.55(1H, d,J=1.2 Hz), 3.66(1H,d,J=1.2 Hz), 4.53(2H,d,J=5.8 Hz), 4.93(1H,ddd,J=6.4,8.3,8.6 Hz), 7.10–7.65(9H,m), 8.91(1H, d,J=8.3 Hz) 9.06(1H,t,J=5.8 Hz), 12.31(1H,s). Mass (FAB (+)) m/e: 436 (MH)$^+$.

Example 58

N-{L-3-trans-{[4-(Pyrimidin-2-yl)piperazin-1-yl]carbonyl}oxirane-2-carbonyl}-L-phenylalanine dimethylamide (Compound No. 79):

Following a process similar to the process of Example 1, the title compound (900 mg) was obtained from the compound (1.0 g, 3.3 mmol) obtained in Preparation Example 2 and 1-(2-pyrimidinyl)piperazine dihydrochloride (773 mg, 3.3 mmol).

mp: 167–168.5° C.; $^1$H-NMR (DMSO-d$_6$) δ: 2.80(3H,s), 2.84(1H,dd,J=8.3,13.4 Hz), 2.89(3H,s), 2.96(1H,dd,J=6.3, 13.4 Hz), 3.49–3.62(4H,m), 3.61(1H,d,J=2.0 Hz), 3.68–3.87 (4H,m), 3.89(1H,d,J=2.0 Hz), 4.97(1H,ddd,J=6.3,8.3,8.3 Hz), 6.68(1H,dd,J=4.6,4.6 Hz), 7.18–7.34(5H,m), 8.40(2H, d,J=4.6 Hz), 8.71(1H,d,J=8.3 Hz). Mass (FAB(+)) m/e: 453 (MH)$^+$.

Example 59

N-{L-3-trans-{2-[6-(2,5-Dimethylpyrrol-1-yl)pyridin-2-yl]ethylcarbamoyl}oxirane-2-carbonyl}-L-phenylalanine dimethylamide (Compound No. 82):

Following a process similar to the process of Example 49, the title compound (520 mg, foam) was obtained from the compound (868 mg, 2.24 mmol) obtained in Preparation Example 2 and 6-(2,5-dimethyl- pyrrol-1-yl)-2-(2-aminoethyl)pyridine (460 mg, 2.14 mmol) obtained in accordance with the process described in International Publication No. WO97-09982.

$^1$H-NMR (DMSO-d$_6$) δ: 2.13(6H,s), 2.67(3H,s), 2.88(3H, s), 2.94(1H,dd,J=8.2,13.2 Hz), 3.03(1H,dd,J=6.2,13.2 Hz), 3.23(1H,d,J=1.0 Hz), 3.26(1H,d,J=1.0 Hz), 3.70(2H,m), 5.09(1H,ddd,J=6.2,8.2,8.3 Hz), 5.91(2H,s), 6.82(1H,d,J=8.0 Hz), 7.08–7.16(3H,m), 7.24–7.30(5H,m), 7.76(1H,t,J=7.0 Hz). Mass (FAB(+)) m/e: 504 (MH)$^+$.

Example 60

N-{L-3-trans-[2-(4-Aminosulfonylphenyl)ethylcarbamoyl]oxirane-2-carbonyl}-L-phenylalanine dimethylamide (Compound No. 83):

Following a process similar to the process of Example 49, the title compound (564 mg, foam) was obtained from the compound (919 mg, 3.0 mmol) obtained in Preparation Example 2 and 4-(2-aminoethyl)benzenesulfonamide (571 mg, 2.85 mmol).

$^1$H-NMR (DMSO-d$_6$) δ: 2.78(3H,s), 2.87(3H,s), 2.76–2.84(3H,m), 2.90–2.97(3H,m), 3.39(1H,d,J=2.0 Hz), 3.55(1H,d,J=2.0 Hz), 4.91(1H,ddd,J=6.1,8.1,8.2 Hz), 7.17–7.36(5H,m), 7.39(2H,d,J=8.0 Hz), 7.75(2H,d,J=8.0 Hz), 8.44(1H,t,J=4.0 Hz), 8.87(1H,d,J=8.1 Hz). Mass (FAB (+)) m/e: 489 (MH)$^+$.

Example 61

N-{L-3-trans-[2-(5-Aminopyridin-2-yl)aminoethylcarbamoyl]oxirane-2-carbonyl}-L-phenylalanine dimethylamide (Compound No. 84):

The compound (300 mg, 0.64 mmol) obtained in Example 37 was subjected to catalytic hydrogenation in accordance with a process similar to the process of Example 35 to obtain the title compound (130 mg, foam).

$^1$H-NMR (DMSO-d$_6$) δ: 2.79(3H,s), 2.82(1H,dd,J=8.3, 13.2 Hz), 2.88(3H,s), 2.95(1H,dd,J=6.1,13.2 Hz), 3.16–3.26 (4H,m), 3.41(1H,d,J=1.0 Hz), 3.59(1H,d,J=1.0 Hz), 4.33 (2H,br.s), 4.91(1H,ddd,J=6.1,8.2,8.3 Hz), 5.73(1H,br.s), 6.30(1H,d,J=8.6 Hz), 6.83(1H,dd,J=2.4,8.6 Hz), 7.16–7.33 (5H,m), 7.46(1H,d,J=2.4 Hz), 8.54(1H,t,J=5.1 Hz), 8.87(1H, d,J=8.2 Hz). Mass (FAB(+)) m/e: 441 (MH)$^+$.

Example 62

N-{L-3-trans-[3-Morpholinopropylcarbamoyl]oxirane-2-carbonyl}-L-phenylalanine dimethylamide (Compound No. 85):

Following a process similar to the process of Example 49, the title compound (1.5 g, foam) was obtained from the compound (2.14 g, 7.0 mmol) obtained in Preparation Example 2 and 4-(3-aminopropyl)morpholine (959 mg, 6.65 mmol).

$^1$H-NMR (CDCl$_3$) δ: 1.65(4H,br.s), 2.67(3H,s), 2.89(3H, s), 2.43–2.49(2H,m), 2.97(2H,br.s), 3.35(1H,d,J=2.0 Hz), 3.38(1H,d,J=2.0 Hz), 3.26–3.45(3H,m), 3.67–3.78(5H,m), 5.10–5.12(1H,m), 6.91(1H,d,J=8.0 Hz), 7.13–7.30(5H,m), 7.73(1H,br.s). Mass (FAB(+)) m/e: 433 (MH)$^+$.

Example 63

N-{L-3-trans-[2-(4-Acetoamidinophenyl)ethylcarbamoyl]oxirane-2-carbonyl}-L-phenylalanine dimethylamide hydrobromide (Compound No. 86):

Following a process similar to the process of Example 49, the title compound (1.8 g, foam) was obtained from the compound (1.78 g, 5.81 mmol) obtained in Preparation Example 2 and N-[4-(2-aminoethyl)phenyl]acetamidine hydrobromide (1.5 g, 5.81 mmol) obtained in accordance with the process described in International Publication No. WO96-19440.

$^1$H-NMR (DMSO-d$_6$) δ: 2.51(3H,s), 2.78(3H,s), 2.87(3H, s), 2.75–2.80(1H,m), 2.90–2.94(2H,m), 2.94–2.98(1H,m), 3.04–3.07(2H,m), 3.40(1H,d,J=2.0 Hz), 3.56(1H,d,J=2.0 Hz), 4.91–4.93(1H,m), 6.92–6.97(1H,m), 7.14–7.38(9H,m), 8.85(1H,d,J=8.1 Hz). Mass (FAB(+)) m/e: 466 (MH)$^+$.

Example 64

N-{L-3-trans-[2-(2-Methyl-5-nitroimidazol-1-yl)ethylcarbamoyl]oxirane-2-carbonyl}-L-phenylalanine dimethylamide (Compound No. 87):

Following a process similar to the process of Example 53, the title compound (450 mg, foam) was obtained from the compound (1.13 g, 2.65 mmol) obtained in Preparation Example 21 and the compound (450 mg, 2.65 mmol) obtained in Preparation Example 28.

$^1$H-NMR (DMSO-d$_6$) δ: 2.39(3H,s), 2.79(3H,s), 2.81(1H, dd,J=8.3,13.4 Hz), 2.87(3H,s), 2.94(1H,dd,J=6.1,13.4 Hz), 3.35(1H,s), 3.41–3.53(2H,m), 3.48(1H,s), 4.33(1H,t,J=5.8 Hz), 4.91(1H,ddd,J=6.1,8.3,8.3 Hz), 7.19–7.30(5H,m), 8.04 (1H,s), 8.51(1H,t,J=6.1 Hz), 8.85(1H,d,J=8.3 Hz). Mass (FAB(+)) m/e: 459 (MH)$^+$.

Example 65

N-{L-3-trans-[2-(Pyrazin-2-yl)ethylcarbamoyl]oxirane-2-carbonyl}-L-phenylalanine dimethylamide (Compound No. 88):

Following a process similar to the process of Example 53, the title compound (1.0 g, foam) was obtained from the compound (1.41 g, 3.3 mmol) obtained in Preparation Example 21 and 2-(2-aminoethyl)pyrazine (400 mg, 3.25 mmol) obtained in accordance with the process described in J. Org. Chem., 30, 4379 (1965).

$^1$H-NMR (DMSO-d$_6$) δ: 2.78(3H,s), 2.81(1H,dd,J=8.5, 13.6 Hz), 2.87(3H,s), 2.89–2.98(1H,m), 2.93(2H,t,J=7.1 Hz), 3.38(1H,d,J=1.8 Hz), 3.45–3.52(2H,m), 3.54(1H,d,J= 1.8 Hz), 4.90(1H,m), 7.17–7.31(5H,m), 8.43(1H,t,J=5.6 Hz), 8.47–8.62(3H,m), 8.87(1H,d,J=8.0 Hz). Mass (FAB (+)) m/e: 412 (MH)$^+$.

Example 66
N-{L-3-trans-[4-(4-Aminopyrimidin-2-yl)piperazin-1-yl]carbamoyl]oxirane-2-carbonyl}-L-phenylalanine dimethylamide (Compound No. 90):

Following a process similar to the process of Example 56, the title compound (216 mg, foam) was obtained from the compound (171 mg, 0.55 mmol) obtained in Preparation Example 2 and 2-(1-piperazinyl)-4-aminopyrimidine (100 mg, 0.55 mmol) obtained in accordance with the process described in Japanese Patent Application Laid-Open No. 81375/1987.

$^1$H-NMR (DMSO-d$_6$) δ: 2.80(3H,s), 2.88(3H,ms), 2.85 (1H,dd,J=8.2,13.3 Hz), 2.96(1H,dd,J=6.2,13.3 Hz), 3.45–3.58(4H,m), 3.60(1H,d,J=2.0 Hz), 3.62–3.68(2H,m), 3.69–3.75(2H,m), 3.87(1H,d,J=2.0 Hz), 4.96(1H,ddd,J=6.2, 8.2,8.2 Hz), 5.76(1H,d,J=5.6 Hz), 6.48(2H,s), 7.22–7.31 (5H,m), 7.76(1H,d,J=5.6 Hz), 8.71(1H,d,J=8.3 Hz). Mass (FAB(+)) m/e: 468 (MH)$^+$.

Example 67
N-{L-3-trans-[2-(4-Aminopyrimidin-2-yl)aminoethylcarbamoyl]oxirane-2-carbonyl}-L-phenylalanine dimethylamide (Compound No. 93):

Following a process similar to the process of Example 53, the title compound (1.0 g) was obtained from the compound (1.28 g, 3.0 mmol) obtained in Preparation Example 21 and the compound (410 mg, 2.67 mmol) obtained in Preparation Example 29.

mp: 190° C. (decomposed).; $^1$H-NMR (DMSO-d$_6$) δ: 2.79(3H,s), 2.81(1H,dd,J=8.6,13.4 Hz), 2.88(3H,s), 2.94 (1H,dd,J=6.1,13.4 Hz), 3.17–3.48(4H,m), 3.39(1H,s), 3.58 (1H,s), 4.91(1H,ddd,J=6.1,8.6,8.7 Hz), 5.70(1H,d,J=5.6 Hz), 6.29(2H.br.s), 6.35(1H,br.s), 7.18–7.33(5H,m), 7.66 (1H,d,J=5.6 Hz), 8.44(1H,t,J=5.4 Hz), 8.86(1H,d,J=8.7 Hz). Mass (FAB(+)) m/e: 442 (MH)$^+$.

Test Example 1
Determination of inhibition activity against cathepsin L and cathepsin B:

Cathepsin L that extracted from a rat liver and completely purified in accordance with the method described in J. Biochem., 84, 650–671 (1978) was used, and as a substrate thereof, Z-Phe-Arg-MCA was used.

One that extracted from a rat liver and completely purified in accordance with the method described in Biochem. Biophys. Res. Commun., 83, 513–520 (1978) was used as cathepsin B, and as a substrate thereof, Z-Arg-Arg-MCA was used.

Each cathepsin was diluted with a diluent (0.1% Brij 35) to adjust its concentration to 0.3 U (0.1 U: a concentration at which 1.0 nmol of MCA is released per minute at 37° C.). An activator/buffer (340 mM sodium acetate, 60 mM acetic acid, 4 mM disodium EDTA; pH 5.5; 250 μl) was added to the solution (500 μl). After the mixture was incubated for 1 minute at 30° C., a specimen solution of the predetermined concentration and a substrate solution (20 ml) were added to conduct a reaction for 10 minutes. The reaction was stopped with a reaction terminator (100 mM sodium monochloroacetate, 30 ml sodium acetate, 70 ml acetic acid; pH 4.3; 1 ml) to determine the fluorescence intensity of aminomethylcoumarin isolated under fluorescence 460 nm in wavelength obtained by excitation at a wavelength of 370 nm using a fluorometer. As a result, as shown in Table 9, it is understood that the invention compounds each have stronger inhibitory activity against cathepsin L than against cathepsin B.

TABLE 9

| Compound No. | IC$_{50}$ (M) Cathepsin L | Cathepsin B |
|---|---|---|
| 6 | 2.0 × 10$^{-7}$ | >10$^{-4}$ |
| 8 | <10$^{-7}$ | >10$^{-4}$ |
| 9 | 8.5 × 10$^{-7}$ | >10$^{-4}$ |
| 11 | 2.4 × 10$^{-6}$ | No inhibition |
| 12 | 2.5 × 10$^{-9}$ | >10$^{-5}$ |
| 15 | 2.2 × 10$^{-7}$ | >10$^{-4}$ |
| 18 | 2.9 × 10$^{-7}$ | >10$^{-4}$ |
| 20 | 6.7 × 10$^{-7}$ | >10$^{-4}$ |
| 22 | 4.7 × 10$^{-7}$ | >10$^{-4}$ |
| 29 | 2.2 × 10$^{-9}$ | >10$^{-4}$ |
| 37 | 4.5 × 10$^{-8}$ | >10$^{-4}$ |
| 39 | 3.5 × 10$^{-7}$ | >10$^{-4}$ |
| 41 | 3.3 × 10$^{-8}$ | >10$^{-5}$ |
| 44 | 6.0 × 10$^{-9}$ | 7.7 × 10$^{-5}$ |
| 46 | 3.4 × 10$^{-8}$ | 8.5 × 10$^{-5}$ |
| 48 | 6.0 × 10$^{-8}$ | 4.5 × 10$^{-5}$ |
| 56 | 4.7 × 10$^{-8}$ | >10$^{-5}$ |
| 62 | <10$^{-9}$ | >10$^{-4}$ |
| 73 | 9.4 × 10$^{-8}$ | No inhibition |
| 77 | 8.2 × 10$^{-8}$ | >10$^{-5}$ |
| 86 | 4.6 × 10$^{-8}$ | >10$^{-5}$ |
| 90 | 9.7 × 10$^{-8}$ | >10$^{-5}$ |
| Prep. Ex. 30 | 8.1 × 10$^{-10}$ | 2.3 × 10$^{-8}$ |

INDUSTRIAL APPLICABILITY

The epoxysuccinamide derivatives or the salts thereof according to the present invention each have inhibitory activity against cysteine proteases such as cathepsins L, B and H and particularly have specific inhibitory activity for cathepsin L, and can hence be used as agents for preventing and treating muscular dystrophy, muscular atrophy, myocardial infarction, apoplectic stroke, Alzheimer disease, disturbance of consciousness and dyskinesis upon head injury, multiple sclerosis, peripheral nerve neuropathy, cataract, inflammation, allergy, fulminant hepatitis, osteoporosis, hypercalcemia, breast cancer, prostatic cancer and prostatic hypertrophy, or agents for inhibiting cancerous proliferation and preventing metastasis and platelet aggregation inhibitors. In particular, they are useful as agents for preventing and treating osteopathy, particularly, osteoporosis.

We claim:
1. An epoxysuccinamide compound represented by a formula (I):

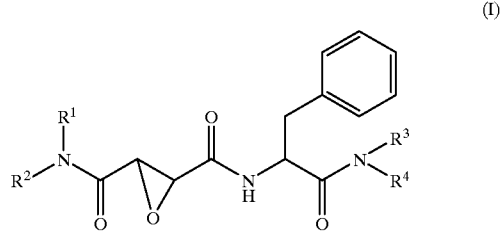

wherein R$^1$ represents a hydrogen atom, an alkyl group or an aminoalkyl group which may have a protecting group, R$^2$ represents an aminoalkyl group which may be substituted, an aryl group which may be substituted, an aralkyl group which may be substituted, a heterocyclic group which may be substituted, or an alkyl group substituted by a heterocyclic ring which may be substituted, or R$^1$ and R$^2$ may form a nitrogen-containing heterocyclic ring, which may be substituted, together with the adjacent nitrogen atoms, and R$^3$ and R$^4$ are the same or different from each other and independently represent a hydrogen atom, an aralkyl group or an unsubstituted alkyl group, or a salt thereof.

2. The compound or the salt thereof according to claim 1, wherein $R^1$ is a hydrogen atom, or a $C_{1-6}$ alkyl or amino-$C_{1-6}$-alkyl group; $R^2$ is an amino-$C_{1-6}$-alkyl group which may be substituted, a phenyl group which may be substituted, a heterocyclic group which may be substituted, a phenyl-$C_{1-6}$-alkyl group which may be substituted, or a $C_{1-6}$ alkyl group substituted by a heterocyclic ring which may be substituted, or $R^1$ and $R^2$ form a nitrogen-containing heterocyclic ring, which may be substituted, together with the adjacent nitrogen atom; and $R^3$ and $R^4$ are the same or different from each other and are independently a hydrogen atom, or a $C_{1-6}$ alkyl or phenyl-$C_{1-6}$-alkyl group.

3. The compound or the salt thereof according to claim 1 or 2, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group which may be substituted by groups selected from a carboxyl group, aralkyloxycarbonyl groups having 8 to 14 carbon atoms in total, $C_{1-6}$ alkyl groups substituted by alkyloxycarbonylamino groups having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl, carbamoyl and amino groups; (4) a saturated or unsaturated heterocyclic group which may be substituted by a phenyl-$C_{1-6}$-alkyl or $C_{1-6}$-alkyl group and has a 5- to 10-membered monocyclic or fused ring having, as heteroatom(s), 1 to 3 atoms selected from nitrogen, oxygen and sulfur; and (5) a $C_{1-6}$ alkyl group substituted by a nitrogen-containing saturated heterocyclic ring or an aromatic heterocyclic ring composed of a 5- to 10-membered monocyclic or fused ring having, as heteroatom(s), 1 to 3 atoms selected from nitrogen, oxygen and sulfur (which the aromatic heterocyclic ring may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylenedioxyphenyl-$C_{1-6}$-alkyl, pyrimidinyl and aminopyrimidinyl groups.

4. The compound or the salt thereof according to claim 1 or 2, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group substituted by groups selected from a carboxyl group, aralkyloxycarbonyl groups having 8 to 14 carbon atoms in total, $C_{1-6}$ alkyl groups substituted by an alkyloxycarbonylamino group having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl and amino groups; (4) a heterocyclic group selected from piperidinyl, pyridyl, quinolyl and isoxazolyl groups which may be substituted by a phenyl-$C_{1-6}$-alkyl group or $C_{1-6}$ alkyl group; and (5) a $C_{1-6}$ alkyl group substituted by a heterocyclic group selected from piperidinyl, morpholino, thiazolyl, imidazolyl, pyridyl, pyrazinyl and benzimidazolyl groups (which may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylenedioxyphenyl-$C_{1-6}$-alkyl, pyrimidinyl and aminopyrimidinyl groups.

5. A composition comprising as an active ingredient a compound or salt thereof represented by formula I:

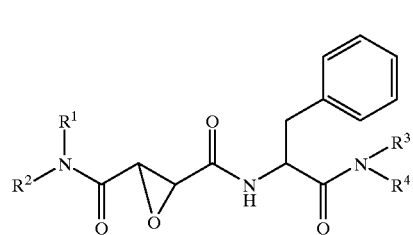

(I)

wherein $R^1$ represents a hydrogen atom, an alkyl group or an aminoalkyl group which may have a protecting group), $R^2$ represents an aminoalkyl group which may be substituted, an aryl group which may be substituted, an aralkyl group which may be substituted, a heterocyclic group which may be substituted, or an alkyl group substituted by a heterocyclic ring which may be substituted, or $R^1$ and $R^2$ may form a nitrogen-containing heterocyclic ring, which may be substituted, together with the adjacent nitrogen atom, and $R^3$ and $R^4$ are the same or different from each other and independently represent a hydrogen atom, an aralkyl group or an unsubstituted alkyl group, or a salt thereof.

6. The composition according to claim 5, which is a cysteine protease inhibitor.

7. The composition according to claim 5, which is an agent for preventing and treating osteopathy.

8. The composition according to claim 7, wherein the osteopathy is osteoporosis.

9. The composition according to claim 5, 6, 7, or 8 further comprising a pharmaceutically acceptable carrier.

10. A process for preparing an epoxysuccinamide compound represented by a formula (I):

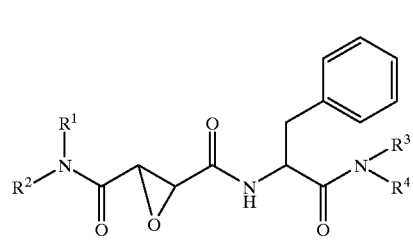

(I)

wherein $R^1$ represents a hydrogen atom, an alkyl group or an aminoalkyl group which may have a protecting group, $R^2$ represents an aminoalkyl group which may be substituted, an aryl group which may be substituted, an aralkyl group which may be substituted, a heterocyclic group which may be substituted, or an alkyl group substituted by a heterocyclic ring which may be substituted, or $R^1$ and $R^2$ may form a nitrogen-containing heterocyclic ring, which may be substituted, together with the adjacent nitrogen atom, and $R^3$ and $R^4$ are the same or different from each other and independently represent a hydrogen atom, an aralkyl group or an unsubstituted alkyl group, or a salt thereof, the process comprising reacting a compound represented by a formula (V):

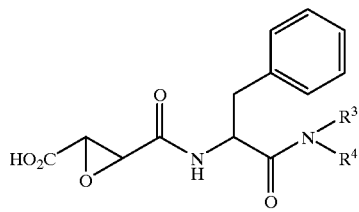

wherein $R^3$ and $R^4$ have the same meanings as defined above, with an amine derivative represented by a formula (VI):

wherein $R^1$ has the same meaning as defined above, and $R^5$ is the same group as $R^2$, or when $R^2$ has a substituent group which takes part in the reaction, $R^5$ represents a group having a protecting group for the substituent group, and optionally eliminating the protecting group of $R^5$.

11. The composition according to claim 5, wherein $R^1$ is a hydrogen atom, or a $C_{1-6}$ alkyl or amino-$C_{1-6}$-alkyl group; $R^2$ is an amino-$C_{1-6}$-alkyl group which may be substituted, a phenyl group which may be substituted, a heterocyclic group which may be substituted, a phenyl-$C_{1-6}$-alkyl group which may be substituted, or a $C_{1-6}$ alkyl group substituted by a heterocyclic ring which may be substituted, or $R^1$ and $R^2$ form a nitrogen-containing heterocyclic ring, which may be substituted, together with the adjacent nitrogen atom; and $R^3$ and $R^4$ are the same or different from each other and independently are a hydrogen atom, or a $C_{1-6}$ alkyl or phenyl-$C_{1-6}$-alkyl group.

12. The composition according to claim 5 or 11, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group which may be substituted by groups selected from a carboxyl group, aralkyloxycarbonyl groups having 8 to 14 carbon atoms in total, $C_{1-6}$ alkyl groups substituted by alkyloxycarbonylamino groups having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl, carbamoyl and amino groups; (4) a saturated or unsaturated heterocyclic group which may be substituted by a phenyl-$C_{1-6}$-alkyl or $C_{1-6}$-alkyl group and has a 5- to 10-membered monocyclic or fused ring having, as heteroatom(s), 1 to 3 atoms selected from nitrogen, oxygen and sulfur; and (5) a $C_{1-6}$ alkyl group substituted by a nitrogen-containing saturated heterocyclic ring or an aromatic heterocyclic ring composed of a 5- to 10-membered monocyclic or fused ring having, as heteroatom(s), 1 to 3 atoms selected from nitrogen, oxygen and sulfur (which the aromatic heterocyclic ring may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylene-dioxyphenyl-$C_{1-6}$-alkyl, pyrimidinyl and aminopyrimidinyl groups.

13. The composition according to claim 5 or 11, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group substituted by groups selected from a carboxyl group, aralkyloxycarbonyl groups having 8 to 14 carbon atoms in total, $C_{1-6}$ alkyl groups substituted by an alkyloxycarbonylamino groups having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl and amino groups; (4) a heterocyclic group selected from piperidinyl, pyridyl, quinolyl and isoxazolyl groups which may be substituted by a phenyl-$C_{1-6}$-alkyl group or $C_{1-6}$ alkyl group; and (5) a $C_{1-6}$ alkyl group substituted by a heterocyclic group selected from piperidinyl, morpholino, thiazolyl, imidazolyl, pyridyl, pyrazinyl and benzimidazolyl groups (which may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylenedioxyphenyl-$C_{1-6}$-alkyl, pyrimidinyl and aminopyrimidinyl groups.

14. A method of treating or preventing osteopathy comprising administering to a subject an effective amount of a composition comprising as an active ingredient a compound or salt thereof represented by formula I:

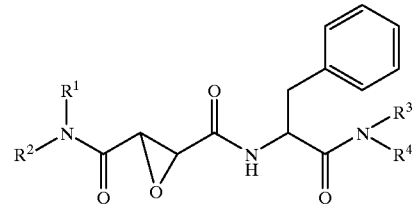

wherein $R^1$ represents a hydrogen atom, an alkyl group or an aminoalkyl group which may have a protecting group, $R^2$ represents an aminoalkyl group which may be substituted, an aryl group which may be substituted, an aralkyl group which may be substituted, a heterocyclic group which may be substituted, or an alkyl group substituted by a heterocyclic ring which may be substituted, or $R^1$ and $R^2$ may form a nitrogen-containing heterocyclic ring, which may be substituted, together with the adjacent nitrogen atom, and $R^3$ and $R^4$ are the same or different from each other and independently represent a hydrogen atom, an aralkyl group or an unsubstituted alkyl group, or a salt thereof.

15. The method according to claim 14, wherein $R^1$ is a hydrogen atom, or a $C_{1-6}$ alkyl or amino-$C_{1-6}$-alkyl group; $R^2$ is an amino-$C_{1-6}$-alkyl group which may be substituted, a phenyl group which may be substituted, a heterocyclic group which may be substituted, a phenyl-$C_{1-6}$-alkyl group which may be substituted, or a $C_{1-6}$ alkyl group substituted by a heterocyclic ring which may be substituted, or $R^1$ and $R^2$ form a nitrogen-containing heterocyclic ring, which may be substituted, together with the adjacent nitrogen atom; and $R^3$ and $R^4$ are the same or different from each other and are independently a hydrogen atom, or a $C_{1-6}$ alkyl or phenyl-$C_{1-6}$-alkyl group.

16. The method according to claim 14 or 15, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group which may be substituted by groups selected from a carboxyl group, aralkyloxycarbonyl groups having 8 to 14 carbon atoms in total, $C_{1-6}$ alkyl groups substituted by alkyloxycarbonylamino groups having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl, carbamoyl and amino groups; (4) a saturated or unsaturated heterocyclic group which may be substituted by a phenyl-$C_{1-6}$-alkyl or $C_{1-6}$-alkyl group and has a 5- to 10-membered monocyclic or fused ring having, as heteroatom(s), 1 to 3 atoms selected from nitrogen, oxygen and sulfur; and (5) a $C_{1-6}$ alkyl group substituted by a nitrogen-containing saturated heterocyclic ring or an aromatic heterocyclic ring composed of a 5- to 10-membered monocyclic or fused ring having, as heteroatom(s), 1 to 3 atoms selected from nitrogen, oxygen and sulfur (which the aromatic heterocyclic ring may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylene-dioxyphenyl-$C_{1-6}$-alkyl, pyrimidinyl and aminopyrimidinyl groups.

17. The method according to claim 14 or 15, wherein $R^2$ is a group selected from (1) an $C_{1-6}$ aminoalkyl group substituted by an alkyloxycarbonyl group having 2 to 7 carbon atoms in total, an aralkyloxycarbonyl group having 8 to 14 carbon atoms in total, a benzenesulfonyl group, or a heterocyclic group (which may be substituted further by an amino or nitro group); (2) a phenyl group substituted by groups selected from a carboxyl group, aralkyloxycarbonyl groups having 8 to 14 carbon atoms in total, $C_{1-6}$ alkyl groups substituted by an alkyloxycarbonylamino group having 2 to 7 carbon atoms in total, acylamino-$C_{1-6}$-alkyl groups, $C_{1-6}$ aminoalkyl groups, an aminosulfonyl group, aryloxy groups having 6 to 10 carbon atoms, $C_{2-6}$ alkenyl groups and $C_{1-6}$ alkyl groups; (3) a phenyl-$C_{1-6}$-alkyl group which may be substituted by a group selected from acetoamidino, methylsulfonyl, aminosulfonyl and amino groups; (4) a heterocyclic group selected from piperidinyl, pyridyl, quinolyl and isoxazolyl groups which may be substituted by a phenyl-$C_{1-6}$-alkyl group or $C_{1-6}$ alkyl group; and (5) a $C_{1-6}$ alkyl group substituted by a heterocyclic group selected from piperidinyl, morpholino, thiazolyl, imidazolyl, pyridyl, pyrazinyl and benzimidazolyl groups (which may be substituted by 1 to 3 groups selected from alkyloxycarbonylamino groups having 2 to 7 carbon atoms in total, an amino group, dialkylpyrrolyl groups, $C_{1-6}$ alkyl groups and a nitro group); or $R^1$ and $R^2$ form, together with the adjacent nitrogen atom, a piperazine ring which may be substituted by a group selected from phenyl, phenyl-$C_{1-6}$-alkyl, methylenedioxyphenyl-$C_{1-6}$-alkyl, pyrimidinyl and aminopyrimidinyl groups.

18. The method according to claim 14 or 15 wherein said composition further comprises a pharmaceutically acceptable carrier.

19. The method according to claim 16 wherein said composition further comprises a pharmaceutically acceptable carrier.

20. The method according to claim 17 wherein said composition further comprises a pharmaceutically acceptable carrier.

21. The method according to claim 14 or 15 wherein said osteopathy is osteoporosis, hyperglycemia, Paget's disease, hyperparathyroidism, or bone metastasis of cancer.

22. The method according to claim 16 wherein said osteopathy is osteoporosis, hyperglycemia, Paget's disease, hyperparathyroidism, or bone metastasis of cancer.

23. The method according to claim 17 wherein said osteopathy is osteoporosis, hyperglycemia, Paget's disease, hyperparathyroidism, or bone metastasis of cancer.

* * * * *